United States Patent [19]
Spinella et al.

[11] Patent Number: 5,866,341
[45] Date of Patent: Feb. 2, 1999

[54] COMPOSITIONS AND METHODS FOR SCREENING DRUG LIBRARIES

[75] Inventors: Dominic Gregory Spinella; Kathleen Ann Becherer; Steven Joel Brown, all of San Diego, Calif.

[73] Assignee: Chugai Pharmaceutical Co., Ltd., Tokyo, Japan

[21] Appl. No.: 627,151

[22] Filed: Apr. 3, 1996

[51] Int. Cl.$^6$ .................................................. G01N 33/53
[52] U.S. Cl. .................................... 435/71; 435/4; 435/5; 435/6; 435/7.2; 435/7.92
[58] Field of Search ................................ 435/4, 5, 6, 7.1, 435/7.2, 7.92

[56] References Cited

U.S. PATENT DOCUMENTS

| | | |
|---|---|---|
| 5,223,408 | 6/1993 | Goeddel et al. . |
| 5,270,170 | 12/1993 | Schatz et al. . |
| 5,338,665 | 8/1994 | Schatz et al. . |
| 5,382,513 | 1/1995 | Lam et al. . |
| 5,427,908 | 6/1995 | Dower et al. . |
| 5,432,018 | 7/1995 | Dower et al. . |
| 5,510,240 | 4/1996 | Lam et al. . |
| 5,514,582 | 5/1996 | Capon et al. . |

FOREIGN PATENT DOCUMENTS

| | | |
|---|---|---|
| 9405394 | 3/1994 | WIPO . |
| 9516209 | 6/1995 | WIPO . |
| 9532425 | 11/1995 | WIPO . |
| 9601688 | 2/1996 | WIPO . |

OTHER PUBLICATIONS

Tawfik, D., et al. cateLISA: A facile general route to catalytic antibodies. 90 *Proc. Natl. Acad. Sci. USA* 373–377 (Jan. 1993).

Akamatsu, Y., et al. Construction of a Human Ig Combinatorial Library from Genomic V Segments and Synthetic CDR3 Fragments. 151(9) *Journal of Immunology* 4651–4659 (Nov. 1, 1993).

Zuckermann, R., et al. Discovery of Nanomolar Ligands for 7–Transmembrane G–Protein–Coupled Receptors from a Diverse N–(Substituted) glycline Peptoid Library. 37 *J. Med. Chem.* 2678–2685 (1994).

Sawyer, J., et al. Rapid detection of antigen binding by antibody fragments expressed in the periplasm of *Escherichia coli*. 4(8) *Protein Engineering* 947–953 (1991).

Houghten, R., et al. Generation and use of synthetic peptide combinatorial libraries for basic research and drug discovery. 354 *Nature* 84–86 (Nov. 7, 1991).

Needels, M., et al. Generation and screening of an oligonucleotide–encoded synthetic peptide library. 90 *Proc. Natl. Acad. Sci. USA* 10700–10704 (Nov. 1993).

Pitti, R., et al. Molecular and Biological Properties of an Interleukin–1 Receptor Immunoadhesin. 31 *Molecular Immunology* 1345–1351 (1994).

Pinilla, C., et al. Rapid Identification of High Affinity Peptide Ligands Using Positional Scanning Synthetic Peptide Combinatorial Libraries. 13(6) *BioTechniques* 901–905 (1992).

Shin, S., et al. Transferrin–antibody fusion proteins are effective in brain targeting. 92 *Proc. Natl. Acad. Sci. USA* 2820–2824 (Mar. 1995).

Baker, D., et al. Control of established experimental allergic encephalomyelitis by inhibition of tumor necrosis factor (TNF) activity within the central nervous system using monoclonal antibodies and TNF receptor–immunoglobin fusion proteins. 24 *Eur. J. Immunol.* 2040–2048 (1994).

Crowe, P., et al. Prodiction of lymphotoxin ( LT$\alpha$ ) and a soluble dimeric form of its receptor using the baculovirus expression system. 168 *J. Immun. Methods.* 79–89 (1994).

Evans, T., et al. Protective Effect of 55–but not 75–kD Soluble Tumor Necrosis Factor Receptor–Immunoglobulin G Fusion Proteins in an Animal Model of Gram–negative Sepsis. 180 *J. Exp. Med.* 2173–2179 (Dec. 1994).

Fountoulakis, M., et al. Interferon γ Receptor Extracellular Domain Expressed as IgG Fusion Protein in Chinese Hamster Ovary Cells. 270(8) *J. Biol. Chem.* 3958–3964 (Feb. 24, 1995).

Tanabe, et al., "Structural and functional analysis of monomorphic determinants recognized by monoclonal antibodies reacting with the HLA class $\alpha_3$ domain", J. Immunol, *148*(10) :3202–3209 May 15, 1992.

*Primary Examiner*—Ponnathapura Achutamurthy
*Attorney, Agent, or Firm*—Christine A. Gritzmacher; Carlos A. Fisher

[57] ABSTRACT

A method of screening for binding partners of a specific molecule. The method employs a chimeric protein having at least two different binding regions; one containing at least a portion of the specific molecule or an analog thereof, and the other containing a binding region of an immunoglobulin chain. In a preferred embodiment, the method is used for rapidly screening member compounds of a combinatorial library for potential biological activity.

63 Claims, No Drawings

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO:1:

AGCTTCGAGC GGCCGCCGTG CCCAGGGATT GTGGTTGTAA G    4 1

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| GATCCTCGAG | TCATTTACCA | GGAGAGTGGG | AGAGGCT | | 37 |
|---|---|---|---|---|---|

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| GATCGGATCC | ATGGGCTCT | CCACCGTGCC | TGAC | 34 |
|---|---|---|---|---|

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| AGCTTCGAGC | GGCCGCTGTG | GTGCCTGAGT | CCTCAGTGCC | 40 |
|---|---|---|---|---|

( 2 ) INFORMATION FOR SEQ ID NO:5:

( i ) SEQUENCE CHARACTERISTICS:
        ( A ) LENGTH: 6253 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| GACGGATCGG | GAGATCTCCC | GATCCCCTAT | GGTCGACTCT | CAGTACAATC | TGCTCTGATG | 60 |
|---|---|---|---|---|---|---|
| CCGCATAGTT | AAGCCAGTAT | CTGCTCCCTG | CTTGTGTGTT | GGAGGTCGCT | GAGTAGTGCG | 120 |
| CGAGCAAAAT | TTAAGCTACA | ACAAGGCAAG | GCTTGACCGA | CAATTGCATG | AAGAATCTGC | 180 |
| TTAGGGTTAG | GCGTTTTGCG | CTGCTTCGCG | ATGTACGGGC | CAGATATACG | CGTTGACATT | 240 |
| GATTATTGAC | TAGTTATTAA | TAGTAATCAA | TTACGGGGTC | ATTAGTTCAT | AGCCCATATA | 300 |
| TGGAGTTCCG | CGTTACATAA | CTTACGGTAA | ATGGCCCGCC | TGGCTGACCG | CCCAACGACC | 360 |
| CCCGCCCATT | GACGTCAATA | ATGACGTATG | TTCCATAGT  | AACGCCAATA | GGGACTTTCC | 420 |
| ATTGACGTCA | ATGGGTGGAC | TATTTACGGT | AAACTGCCCA | CTTGGCAGTA | ATCATATGCC | 480 |
| AAGTACGCCC | CCTATTGACG | TCAATGACGG | TAAATGGCCC | GCCTGGCATT | ATGCCCAGTA | 540 |
| CATGACCTTA | TGGGACTTTC | CTACTTGGCA | GTACATCTAC | GTATTAGTCA | TCGCTATTAC | 600 |
| CATGGTGATG | CGGTTTTGGC | AGTACATCAA | TGGGCGTGGA | TAGCGGTTTG | ACTCACGGGG | 660 |
| ATTTCCAAGT | CTCCACCCCA | TTGACGTCAA | TGGGAGTTTG | TTTTGGCACC | AAAATCAACG | 720 |
| GGACTTTCCA | AAATGTCGTA | ACAACTCCGC | CCCATTGACG | GTAGGCGTGT | ACGGTGGGAG | 780 |
| GTCTATATAA | GCAGAGCTCT | CTGGCTAACT | AGAGAACCCA | CTGCTTACTG | GCTTATCGAA | 840 |
| ATTAATACGA | CTCACTATAG | GGAGACCCAA | GCTGGCTAGC | GTTTAAACTT | AAGCTTGGTA | 900 |
| CCGAGCTCGG | ATCCACTAGT | CCAGTGTGGT | GGAATTCTGC | AGATATCCAG | CACAGTGGCG | 960 |

```
GCCGCCGTGC  CCAGGGATTG  TGGTTGTAAG  CCTTGCATAT  GTACAGGTAA  GTCAGTGGCC    1020
TTCACCTGAC  CCAGATGCAA  CAAGTGGCAA  TGGTTGGAGG  GTGGCCAGGT  ATTGACCTAT    1080
TTCCACCTTT  CTTCTTCATC  CTTAGTCCCA  CTGTCTTCAT  CTTCCCCCCA  AAGCCCAAGG    1140
ATGTGCTCAC  CATTACTCTG  ACTCCTAAGG  TCACGTGTGT  TGTGGTAGAC  ATCAGCAAGG    1200
ATGATCCCGA  GGTCCAGTTC  AGCTGGTTTG  GGAGGTGCAC  ACAGCTCAGA  CGCAACCCCG    1260
GGAGGAGCAG  TTCAACAGCA  CTTTCCGCTC  AGTCAGTGAA  CTTCCCATCA  TGCACCAGGA    1320
CTGGCTCAAT  GGCAAGGAGT  TCAAATGCAG  GGTCAACAGT  GCAGCTTTCC  CTGCCCCCAT    1380
CGAGAAAACC  ATCTCCAAAA  CCAAGGTGA   GAGCTGCAGT  GTGTGACATA  GAAGCTGCAA    1440
TAGTCAGTCC  CTTGGCATAA  CAGACCCCTG  CCCTGTTCGT  GACCTCTGTG  CTGACCAATC    1500
TCTTTACCCA  CCCACAGGCA  GACCGAAGGC  TCCACAGGTG  TACACCATTC  CACCTCCCAA    1560
GGAGCAGATG  GCCAAGGATA  AAGTCAGTCT  GACCGCCATG  ATAACAGACT  TCTTCCCTGA    1620
AGACATTACT  GTGGAGTGGC  AGTGGAATGG  GCAGCCAGCG  GAGAACTACA  AGAACACTCA    1680
GCCCATCATG  AACACGAATG  GCTCTTACTT  CGTCTACAGC  AAGCTCAATG  TGCAGAAGAG    1740
CAACTGGGAG  GCAGGAAATA  CTTTCACCTG  CTCTGTGTTA  CATGAGGGCC  TACACAACCA    1800
CCATACTGAG  AAGAGCCTCT  CCCACTCTCC  TGGTAAATGA  CTCGAGTCTA  GAGGGCCCGT    1860
TTAAACCCGC  TGATCAGCCT  CGACTGTGCC  TTCTAGTTGC  CAGCCATCTG  TTGTTTGCCC    1920
CTCCCCCGTG  CCTTCCTTGA  CCCTGGAAGG  TGCCACTCCC  ACTGTCCTTT  CCTAATAAAA    1980
TGAGGAAATT  GCATCGCATT  GTCTGAGTAG  GTGTCATTCT  ATTCTGGGGG  GTGGGGTGGG    2040
GCAGGACAGC  AAGGGGGAGG  ATTGGGAAGA  CAATAGCAGG  CATGCTGGGG  ATGCGGTGGG    2100
CTCTATGGCT  TCTGAGGCGG  AAAGAACCAG  CTGGGGCTCT  AGGGGGTATC  CCCACGCGCC    2160
CTGTAGCGGC  GCATTAAGCG  CGGCGGGTGT  GGTGGTTACG  CGCAGCGTGA  CCGCTACACT    2220
CTAGCGCCCG  CTCCTTTCGC  TTTCTTCCCT  TCCTTTCTCG  CCACGTTCGC  CGGCTTTCCC    2280
CGTCAAGCTC  TAAATCGGGG  CATCCCTTTA  GGGTTCCGAT  TTAGTGCTTT  ACGGCACCTC    2340
GACCCCAAAA  AACTTGATTA  GGGTGATGGT  TCACGTAGTG  GGCCATCGCC  CTGATAGACG    2400
GTTTTTCGCC  CTTTGACGTT  GGAGTCCACG  TTCTTTAATA  GTGGACTCTT  GTTCCAAACT    2460
GGAACAACAC  TCAACCCTAT  CTCGGTCTAT  TCTTTTGATT  TATAAGGGAT  TTTGGGGATT    2520
TCGGCCTATT  GGTTAAAAAA  TGAGCTGATT  TAACAAAAAT  TTAACGCGAA  TTAATTCTGT    2580
GGAATGTGTG  TCAGTTAGGG  TGTGGAAAGT  CCCCAGGCTC  CCCAGGCAGG  CAGAAGTATG    2640
CAAAGCATGC  ATCTCAATTA  GTCAGCAACC  AGGTGTGGAA  AGTCCCCAGG  CTCCCCAGCA    2700
GGCAGAAGTA  TGCAAAGCAT  GCATCTCAAT  TAGTCAGCAA  CCATAGTCCC  GCCCCTAACT    2760
CCGCCCATCC  CGCCCCTAAC  TCCGCCCAGT  TCCGCCCATT  CTCCGCCCCA  TGGCTGACTA    2820
ATTTTTTTTA  TTTATGCAGA  GGCCGAGGCC  GCCTCTGCCT  CTGAGCTATT  CCAGAAGTAG    2880
TGAGGAGGCT  TTTTTGGAGG  CCTAGGCTTT  TGCAAAAAGC  TCCCGGGAGC  TTGTATATCC    2940
ATTTTCGGAT  CTGATCAAGA  GACAGGATGA  GGATCGTTTC  GCATGATTGA  ACAAGATGGA    3000
TTGCACGCAG  GTTCTCCGGC  CGCTTGGGTG  GAGAGGCTAT  TCGGCTATGA  CTGGGCACAA    3060
CAGACAATCG  GCTGCTCTGA  TGCCGCCGTG  TTCCGGCTGT  CAGCGCAGGG  GCGCCCGGTT    3120
CTTTTTGTCA  AGACCGACCT  GTCCGGTGCC  CTGAATGAAC  TGCAGGACGA  GGCAGCGCGG    3180
CTATCGTGGC  TGGCCACGAC  GGGCGTTCCT  TGCGCAGCTG  TGCTCGACGT  TGTCACTGAA    3240
GCGGGAAGGG  ACTGGCTGCT  ATTGGGCGAA  GTGCCGGGGC  AGGATCTCCT  GTCATCTCAC    3300
CTTGCTCCTG  CCGAGAAAGT  ATCCATCATG  GCTGATGCAA  TGCGGCGGCT  GCATACGCTT    3360
```

```
GATCCGGCTA  CCTGCCCATT  CGACCACCAA  GCGAAACATC  GCATCGAGCG  AGCACGTACT  3420
CGGATGGAAG  CCGGTCTTGT  CGATCAGGAT  GATCTGGACG  AAGAGCATCA  GGGGCTCGCG  3480
CCAGCCGAAC  TGTTCGCCAG  GCTCAAGGCG  CGCATGCCCG  ACGGCGAGGA  TCTCGTCGTG  3540
ACCCATGGCG  ATGCCTGCTT  GCCGAATATC  ATGGTGGAAA  ATGGCCGCTT  TTCTGGATTC  3600
ATCGACTGTG  GCCGGCTGGG  TGTGGCGGAC  CGCTATCAGG  ACATAGCGTT  GGCTACCCGT  3660
GATATTGCTG  AAGAGCTTGG  CGGCGAATGG  GCTGACCGCT  TCCTCGTGCT  TTACGGTATC  3720
GCCGCTCCCG  ATTCGCAGCG  CATCGCCTTC  GAGTTCTTCT  GAGCGGGACT  CTGGGGTTCG  3780
AAATGACCGA  CCAAGCGACG  CCCAACCTGC  CATCACGAGA  TTTCGATTCC  ACCGCCGCCT  3840
TCTATGAAAG  GTTGGGCTTC  GGAATCGTTT  TCCGGGACGC  CGGCTGGATG  ATCCTCCAGC  3900
GCGGGGATCT  CATGCTGGAG  TTCTTCGCCC  ACCCCAACTT  GTTTATTGCA  GCTTATAATG  3960
GTTACAAATA  AAGCAATAGC  ATCACAAATT  TCACAAATAA  AGCATTTTTT  TCACTGCATT  4020
CTAGTTGTGG  TTTGTCCAAA  CTCATCAATG  TATCTTATCA  TGTCTGTATA  CCGTCGACCT  4080
CTAGCTAGAG  CTTGGCGTAA  TCATGGTCAT  AGCTGTTTCC  TGTGTGAAAT  TGTTATCCGC  4140
TCACAATTCC  ACACAACATA  CGAGCCGGAA  GCATAAAGTG  TAAAGCCTGG  GGTGCCTAAT  4200
GAGTGAGCTA  ACTCACATTA  ATTGCGTTGC  GCTCACTGCC  CGCTTTCCAG  TCGGGAAACC  4260
TGTCGTGCCA  GCTGCATTAA  TGAATCGGCC  AACGCGCGGG  GAGAGGCGGT  TTGCGTATTG  4320
GGCGCTCTTC  CGCTTCCTCG  CTCACTGACT  CGCTGCGCTC  GGTCGTTCGG  CTGCGGCGAG  4380
CGGTATCAGC  TCACTCAAAG  GCGGTAATAC  GGTTATCCAC  AGAATCAGGG  GATAACGCAG  4440
GAAAGAACAT  GTGAGCAAAA  GGCCAGCAAA  AGGCCAGGAA  CCGTAAAAAG  GCCGCGTTGC  4500
TGGCGTTTTT  CCATAGGCTC  CGCCCCCCTG  ACGAGCATCA  CAAAAATCGA  CGCTCAAGTC  4560
AGAGGTGGCG  AAACCCGACA  GGACTATAAA  GATACCAGGC  GTTTCCCCCT  GGAAGCTCCC  4620
TCGTGCGCTC  TCCTGTTCCG  ACCCTGCCGC  TTACCGGATA  CCTGTCCGCC  TTTCTCCCTT  4680
CGGGAAGCGT  GGCGCTTTCT  CAATGCTCAC  GCTGTAGGTA  TCTCAGTTCG  GTGTAGGTCG  4740
TTCGCTCCAA  GCTGGGCTGT  GTGCACGAAC  CCCCCGTTCA  GCCCGACCGC  TGCGCCTTAT  4800
CCGGTAACTA  TCGTCTTGAG  TCCAACCCGG  TAAGACACGA  CTTATCGCCA  CTGGCAGCAG  4860
CCACTGGTAA  CAGGATTAGC  AGAGCGAGGT  ATGTAGGCGG  TGCTACAGAG  TTCTTGAAGT  4920
GGTGGCCTAA  CTACGGCTAC  ACTAGAAGGA  CAGTATTTGG  TATCTGCGCT  CTGCTGAAGC  4980
CAGTTACCTT  CGGAAAAAGA  GTTGGTAGCT  CTTGATCCGG  CAAACAAACC  ACCGCTGGTA  5040
GCGGTGGTTT  TTTTGTTTGC  AAGCAGCAGA  TTACGCGCAG  AAAAAAAGGA  TCTCAAGAAG  5100
ATCCTTTGAT  CTTTTCTACG  GGGTCTGACG  CTCAGTGGAA  CGAAAACTCA  CGTTAAGGGA  5160
TTTTGGTCAT  GAGATTATCA  AAAAGGATCT  TCACCTAGAT  CCTTTTAAAT  TAAAAATGAA  5220
GTTTTAAATC  AATCTAAAGT  ATATATGAGT  AAACTTGGTC  TGACAGTTAC  CAATGCTTAA  5280
TCAGTGAGGC  ACCTATCTCA  GCGATCTGTC  TATTTCGTTC  ATCCATAGTT  GCCTGACTCC  5340
CCGTCGTGTA  GATAACTACG  ATACGGGAGG  GCTTACCATC  TGGCCCCAGT  GCTGCAATGA  5400
TACCGCGAGA  CCCACGCTCA  CCGGCTCCAG  ATTTATCAGC  AATAAACCAG  CCAGCCGGAA  5460
GGGCCGAGCG  CAGAAGTGGT  CCTGCAACTT  TATCCGCCTC  CATCCAGTCT  ATTAATTGTT  5520
GCCGGGAAGC  TAGAGTAAGT  AGTTCGCCAG  TTAATAGTTT  GCGCAACGTT  GTTGCCATTG  5580
CTACAGGCAT  CGTGGTGTCA  CGCTCGTCGT  TTGGTATGGC  TTCATTCAGC  TCCGGTTCCC  5640
AACGATCAAG  GCGAGTTACA  TGATCCCCCA  TGTTGTGCAA  AAAAGCGGTT  AGCTCCTTCG  5700
GTCCTCCGAT  CGTTGTCAGA  AGTAAGTTGG  CCGCATCATG  GTTATGGCAG  CACTGCATAA  5760
```

| | | | | | |
|---|---|---|---|---|---|
| TTCTCTTACT | GTCATGCCAT | CCGTAAGATG | CTTTTCTGTG | ACTGGTGAGT | ACTCAACCAA | 5820 |
| GTCATTCTGA | GAATAGTGTA | TGCGGCGACC | GAGTTGCTCT | TGCCCGGCGT | CAATACGGGA | 5880 |
| TAATACCGCG | CCACATAGCA | GAACTTTAAA | AGTGCTCATC | ATTGGAAAAC | GTTCTTCGGG | 5940 |
| GCGAAAACTC | TCAAGGATCT | TACCGCTGTT | GAGATCCAGT | TCGATGTAAC | CCACTCGTGC | 6000 |
| ACCCAACTGA | TCTTCAGCAT | CTTTTACTTT | CACCAGCGTT | TCTGGGTGAG | CAAAAACAGG | 6060 |
| AAGGCAAAAT | GCCGCAAAAA | AGGGAATAAG | GGCGACACGG | AAATGTTGAA | TACTCATACT | 6120 |
| CTTCCTTTTT | CAATATTATT | GAAGCATTTA | TCAGGGTTAT | TGTCTCATGA | GCGGATACAT | 6180 |
| ATTTGAATGT | ATTTAGAAAA | ATAAACAAAT | AGGGGTTCCG | CGCACATTTC | CCCGAAAAGT | 6240 |
| GCCACCTGAC | GTC | | | | | 6253 |

( 2 ) INFORMATION FOR SEQ ID NO:6:

( i ) SEQUENCE CHARACTERISTICS:
        ( A ) LENGTH: 6896 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | | |
|---|---|---|---|---|---|
| GACGGATCGG | GAGATCTCCC | GATCCCCTAT | GGTCGACTCT | CAGTACAATC | TGCTCTGATG | 60 |
| CCGCATAGTT | AAGCCAGTAT | CTGCTCCCTG | CTTGTGTGTT | GGAGGTCGCT | GAGTAGTGCG | 120 |
| CGAGCAAAAT | TTAAGCTACA | ACAAGGCAAG | GCTTGACCGA | CAATTGCATG | AAGAATCTGC | 180 |
| TTAGGGTTAG | GCGTTTTGCG | CTGCTTCGCG | ATGTACGGGC | CAGATATACG | CGTTGACATT | 240 |
| GATTATTGAC | TAGTTATTAA | TAGTAATCAA | TTACGGGGTC | ATTAGTTCAT | AGCCCATATA | 300 |
| TGGAGTTCCG | CGTTACATAA | CTTACGGTAA | ATGGCCCGCC | TGGCTGACCG | CCCAACGACC | 360 |
| CCCGCCCATT | GACGTCAATA | ATGACGTATG | TTCCCATAGT | AACGCCAATA | GGGACTTTCC | 420 |
| ATTGACGTCA | ATGGGTGGAC | TATTTACGGT | AAACTGCCCA | CTTGGCAGTA | CATCAAGTGT | 480 |
| ATCATATGCC | AAGTACGCCC | CCTATTGACG | TCAATGACGG | TAAATGGCCC | GCCTGGCATT | 540 |
| ATGCCCAGTA | CATGACCTTA | TGGGACTTTC | CTACTTGGCA | GTACATCTAC | GTATTAGTCA | 600 |
| TCGCTATTAC | CATGGTGATG | CGGTTTTGGC | AGTACATCAA | TGGGCGTGGA | TAGCGGTTTG | 660 |
| ACTCACGGGG | ATTTCCAAGT | CTCCACCCCA | TTGACGTCAA | TGGGAGTTTG | TTTTGGCACC | 720 |
| AAAATCAACG | GGACTTTCCA | AAATGTCGTA | ACAACTCCGC | CCCATTGACG | CAAATGGGCG | 780 |
| GTAGGCGTGT | ACGGTGGGAG | GTCTATATAA | GCAGAGCTCT | CTGGCTAACT | AGAGAACCCA | 840 |
| CTGCTTACTG | GCTTATCGAA | ATTAATACGA | CTCACTATAG | GGAGACCCAA | GCTGGCTAGC | 900 |
| GTTTAAACTT | AAGCTTGGTA | CCGAGCTCGG | ATCCATGGGC | CTCTCCACCG | TGCCTGACCT | 960 |
| GCTGCTGCCG | CTGGTGCTCC | TGGAGCTGTT | GGTGGGAATA | TACCCCTCAG | GGGTTATTGG | 1020 |
| ACTGGTCCCT | CACCTAGGGG | ACAGGGAGAA | GAGAGATAGT | GTGTGTCCCC | AAGGAAAATA | 1080 |
| TATCCACCCT | CAAAATAATT | CGATTTGCTG | TACCAAGTGC | CACAAAGGAA | CCTACTTGTA | 1140 |
| CAATGACTGT | CCAGGCCCGG | GGCAGGATAC | GGACTGCAGG | GAGTGTGAGA | GCGGCTCCTT | 1200 |
| CACCGCTTCA | GAAAACCACC | TCAGACACTG | CCTCAGCTGC | TCCAAATGCC | GAAGGAAAT | 1260 |
| GGGTCAGGTG | GAGATCTCTT | CTTGCACAGT | GGACCGGGAC | ACCGTGTGTG | GCTGCAGGAA | 1320 |
| GAACCAGTAC | CGGCATTATT | GGAGTGAAAA | CCTTTTCCAG | TGCTTCAATT | GCAGCCTCTG | 1380 |
| CCTCAATGGG | ACCGTGCACC | TCTCCTGCCA | GGAGAAACAG | AACACCGTGT | GCACCTGCCA | 1440 |
| TGCAGGTTTC | TTTCTAAGAG | AAAACGAGTG | TGTCTCCTGT | AGTAACTGTA | AGAAAAGCCT | 1500 |

```
GGAGTGCACG  AAGTTGTGCC  TACCCCAGAT  TGAGAATGTT  AAGGGCACTG  AGGACTCAGG  1560

CACCACAGCG  GCCGCCGTGC  CCAGGGATTG  TGGTTGTAAG  CCTTGCATAT  GTACAGGTAA  1620

GTCAGTGGCC  TTCACCTGAC  CCAGATGCAA  CAAGTGGCAA  TGGTTGGAGG  GTGGCCAGGT  1680

ATTGACCTAT  TTCCACCTTT  CTTCTTCATC  CTTAGTCCCA  GAAGTATCAT  CTGTCTTCAT  1740

CTTCCCCCCA  AAGCCCAAGG  ATGTGCTCAC  CATTACTCTG  ACTCCTAAGG  TCACGTGTGT  1800

TGTGGTAGAC  ATCAGCAAGG  ATGATCCCGA  GGTCCAGTTC  AGCTGGTTTG  TAGATGATGT  1860

GGAGGTGCAC  ACAGCTCAGA  CGCAACCCCG  GGAGGAGCAG  TTCAACAGCA  CTTTCCGCTC  1920

AGTCAGTGAA  CTTCCCATCA  TGCACCAGGA  CTGGCTCAAT  GGCAAGGAGT  TCAAATGCAG  1980

GGTCAACAGT  GCAGCTTTCC  CTGCCCCCAT  CGAGAAAACC  ATCTCCAAAA  CCAAAGGTGA  2040

GAGCTGCAGT  GTGTGACATA  GAAGCTGCAA  TAGTCAGTCC  ATAGACAGAG  CTTGGCATAA  2100

CAGACCCCTG  CCCTGTTCGT  GACCTCTGTG  CTGACCAATC  TCTTTACCCA  CCCACAGGCA  2160

GACCGAAGGC  TCCACAGGTG  TACACCATTC  CACCTCCCAA  GGAGCAGATG  GCCAAGGATA  2220

AAGTCAGTCT  GACCGCCATG  ATAACAGACT  TCTTCCCTGA  AGACATTACT  GTGGAGTGGC  2280

AGTGGAATGG  GCAGCCAGCG  GAGAACTACA  AGAACACTCA  GCCCATCATG  AACACGAATG  2340

GCTCTTACTT  CGTCTACAGC  AAGCTCAATG  TGCAGAAGAG  CAACTGGGAG  GCAGGAAATA  2400

CTTTCACCTG  CTCTGTGTTA  CATGAGGGCC  TACACAACCA  CCATACTGAG  AAGAGCCTCT  2460

CCCACTCTCC  TGGTAAATGA  CTCGAGTCTA  GAGGGCCCGT  TTAAACCCGC  TGATCAGCCT  2520

CGACTGTGCC  TTCTAGTTGC  CAGCCATCTG  CCGTGCCTTC  CTTGACCCTG  GAAGGTGCCA  2580

CTCCCACTGT  CCTTTCCTAA  TAAAATGAGG  AAATTGCATC  GCATTGTCTG  AGTAGGTGTC  2640

ATTCTATTCT  GGGGGGTGGG  GTGGGGCAGG  ACAGCAAGGG  GGAGGATTGG  GAAGACAATA  2700

GCAGGCATGC  TGGGGATGCG  GTGGGCTCTA  TGGCTTCTGA  GGCGGAAAGA  ACCAGCTGGG  2760

GCTCTAGGGG  GTATCCCCAC  GCGCCCTGTA  GCGGCGCATT  AAGCGCGGCG  GGTGTGGTGG  2820

TTACGCGCAG  CGTGACCGCT  ACACTTGCCA  GCGCCCTAGC  GCCCGCTCCT  TTCGCTTTCT  2880

TCCCTTCCTT  TCTCGCCACG  TTCGCCGGCT  TTCCCCGTCA  AGCTCTAAAT  CGGGGCATCC  2940

CTTTAGGGTT  CCGATTTAGT  GCTTTACGGC  ACCTCGACCC  CAAAAAACTT  GATTAGGGTG  3000

ATGGTTCACG  TAGTGGGCCA  TCGCCCTGAT  AGACGGTTTT  TCGCCCTTTG  ACGTTGGAGT  3060

CCACGTTCTT  TAATAGTGGA  CTCTTGTTCC  AAACTGGAAC  AACACTCAAC  CCTATCTCGG  3120

TCTATTCTTT  TGATTTATAA  GGGATTTTGG  GGATTTCGGC  CTATTGGTTA  AAAAATGAGC  3180

TGATTTAACA  AAAATTTAAC  GCGAATTAAT  TCTGTGGAAT  GTGTGTCAGT  TAGGGTGTGG  3240

AAAGTCCCCA  GGCTCCCCAG  GCAGGCAGAA  GTATGCAAAG  CATGCATCTC  AATTAGTCAG  3300

CAACCAGGTG  TGGAAAGTCC  CCAGGCTCCC  CAGCAGGCAG  AAGTATGCAA  AGCATGCATC  3360

TCAATTAGTC  AGCAACCATA  GTCCGCCCC  TAACTCCGCC  CATCCGCCC  CTAACTCCGC  3420

CCAGTTCCGC  CCATTCTCCG  CCCCATGGCT  GACTAATTTT  TTTTATTTAT  GCAGAGGCCG  3480

AGGCCGCCTC  TGCCTCTGAG  CTATTCCAGA  AGTAGTGAGG  AGGCTTTTTT  GGAGGCCTAG  3540

GCTTTTGCAA  AAAGCTCCCG  GGAGCTTGTA  TATCCATTTT  CGGATCTGAT  CAAGAGACAG  3600

GATGAGGATC  GTTTCGCATG  ATTGAACAAG  ATGGATTGCA  CGCAGGTTCT  CCGGCCGCTT  3660

GGGTGGAGAG  GCTATTCGGC  TATGACTGGG  CACAACAGAC  AATCGGCTGC  TCTGATGCCG  3720

CCGTGTTCCG  GCTGTCAGCG  CAGGGGCGCC  CGGTTCTTTT  TGTCAAGACC  GACCTGTCCG  3780

GTGCCCTGAA  TGAACTGCAG  GACGAGGCAG  CGCGGCTATC  GTGGCTGGCC  ACGACGGGCG  3840

TTCCTTGCGC  AGCTGTGCTC  GACGTTGTCA  CTGAAGCGGG  AAGGGACTGG  CTGCTATTGG  3900
```

```
GCGAAGTGCC   GGGGCAGGAT   CTCCTGTCAT   CTCACCTTGC   TCCTGCCGAG   AAAGTATCCA    3960
TCATGGCTGA   TGCAATGCGG   CGGCTGCATA   CGCTTGATCC   GGCTACCTGC   CCATTCGACC    4020
ACCAAGCGAA   ACATCGCATC   GAGCGAGCAC   GTACTCGGAT   GGAAGCCGGT   CTTGTCGATC    4080
AGGATGATCT   GGACGAAGAG   CATCAGGGGC   TCGCGCCAGC   CGAACTGTTC   GCCAGGCTCA    4140
AGGCGCGCAT   GCCCGACGGC   GAGGATCTCG   TCGTGACCCA   TGGCGATGCC   TGCTTGCCGA    4200
ATATCATGGT   GGAAAATGGC   CGCTTTTCTG   GATTCATCGA   CTGTGGCCGG   CTGGGTGTGG    4260
CGGACCGCTA   TCAGGACATA   GCGTTGGCTA   CCCGTGATAT   TGCTGAAGAG   CTTGGCGGCG    4320
AATGGGCTGA   CCGCTTCCTC   GTGCTTTACG   GTATCGCCGC   TCCCGATTCG   CAGCGCATCG    4380
CCTTCTATCG   CCTTCTTGAC   GAGTTCTTCT   GAGCGGGACT   CTGGGGTTCG   AAATGACCGA    4440
CCAAGCGACG   CCCAACCTGC   CATCACGAGA   TTTCGATTCC   ACCGCCGCCT   TCTATGAAAG    4500
GTTGGGCTTC   GGAATCGTTT   TCCGGGACGC   CGGCTGGATG   ATCCTCCAGC   GCGGGGATCT    4560
CATGCTGGAG   TTCTTCGCCC   ACCCCAACTT   GTTTATTGCA   GCTTATAATG   GTTACAAATA    4620
AAGCAATAGC   ATCACAAATT   TCACAAATAA   AGCATTTTTT   TCACTGCATT   CTAGTTGTGG    4680
TTTGTCCAAA   CTCATCAATG   TATCTTATCA   TGTCTGTATA   CCGTCGACCT   CTAGCTAGAG    4740
CTTGGCGTAA   TCATGGTCAT   AGCTGTTTCC   TGTGTGAAAT   TGTTATCCGC   TCACAATTCC    4800
ACACAACATA   CGAGCCGGAA   GCATAAAGTG   TAAAGCCTGG   GGTGCCTAAT   GAGTGAGCTA    4860
ACTCACATTA   ATTGCGTTGC   GCTCACTGCC   CGCTTTCCAG   TCGGGAAACC   TGTCGTGCCA    4920
GCTGCATTAA   TGAATCGGCC   AACGCGCGGG   GAGAGGCGGT   TTGCGTATTG   GGCGCTCTTC    4980
CGCTTCCTCG   CTCACTGACT   CGCTGCGCTC   GGTCGTTCGG   CTGCGGCGAG   CGGTATCAGC    5040
TCACTCAAAG   GCGGTAATAC   GGTTATCCAC   AGAATCAGGG   GATAACGCAG   GAAAGAACAT    5100
GTGAGCAAAA   GGCCAGCAAA   AGGCCAGGAA   CCGTAAAAAG   GCCGCGTTGC   TGGCGTTTTT    5160
CCATAGGCTC   CGCCCCCCTG   ACGAGCATCA   CAAAAATCGA   CGCTCAAGTC   AGAGGTGGCG    5220
AAACCCGACA   GGACTGTTTC   CCCTGGAAG    CTCCCTCGTG   CGCTCTCCTG   TTCCGACCCT    5280
GCCGCTTACC   GGATACCTGT   CCGCCTTTCT   CCCTTCGGGA   AGCGTGGCGC   TTTCTCAATG    5340
CTCACGCTGT   AGGTATCTCA   GTTCGGTGTA   GGTCGTTCGC   TCCAAGCTGG   GCTGTGTGCA    5400
CGAACCCCCC   GTTCAGCCCG   ACCGCTGCGC   CTTATCCGGT   AACTATCGTC   TTGAGTCCAA    5460
CCCGGTAAGA   CACGACTTAT   CGCCACTGGC   AGCAGCCACT   GGTAACAGGA   TTAGCAGAGC    5520
GAGGTATGTA   GGCGGTGCTA   CAGAGTTCTT   GAAGTGGTGG   CCTAACTACG   GCTACACTAG    5580
AAGGACAGTA   TTTGGTATCT   GCGCTCTGCT   GAAGCCAGTT   ACCTTCGGAA   AAAGAGTTGG    5640
TAGCTCTTGA   TCCGGCAAAC   AAACCACCGC   TGGTAGCGGT   GGTTTTTTTG   TTTGCAAGCA    5700
GCAGATTACG   CGCAGAAAAA   AAGGATCTCA   AGAAGATCCT   TTGATCTTTT   CTACGGGGTC    5760
TGACGCTCAG   TGGAACGAAA   ACTCACGTTA   AGGGATTTTG   GTCATGAGAT   TATCAAAAAG    5820
GATCTTCACC   TAGATCCTTT   TAAATTAAAA   ATGAAGTTTT   AAATCAATCT   AAAGTATATA    5880
TGAGTAAACT   TGGTCTGACA   GTTACCAATG   CTTAATCAGT   GAGGCACCTA   TCTCAGCGAT    5940
CTGTCTATTT   CGTTCATCCA   TAGTTGCCTG   ACTCCCCGTC   GTGTAGATAA   CTACGATACG    6000
GGAGGGCTTA   CCATCTGGCC   CCAGTGCTGC   AATGATACCG   CGAGACCCAC   GCTCACCGGC    6060
TCCAGATTTA   TCAGCAATAA   ACCAGCCAGC   CGGAAGGGCC   GAGCGCAGAA   GTGGTCCTGC    6120
AACTTTATCC   GCCTCCATCC   AGTCTATTAA   TTGTTGCCGG   GAAGCTAGAG   TAAGTAGTTC    6180
GCCAGTTAAT   AGTTTGCGCA   ACGTTGTTGC   CATTGCTACA   GGCATCGTGG   TGTCACGCTC    6240
GTCGTTTGGT   ATGGCTTCAT   TCAGCTCCGG   TTCCCAACGA   TCAAGGCGAG   TTACATGATC    6300
```

| | | | | | |
|---|---|---|---|---|---|
| CCCCATGTTG | TGCAAAAAAG | CGGTTAGCTC | CTTCGGTCCT | CCGATCGTTG | TCAGAAGTAA 6360 |
| GTTGGCCGCA | GTGTTATCAC | TCATGGTTAT | GGCAGCACTG | CATAATTCTC | TTACTGTCAT 6420 |
| GCCATCCGTA | AGATGCTTTT | CTGTGACTGG | TGAGTACTCA | ACCAAGTCAT | TCTGAGAATA 6480 |
| GTGTATGCGG | CGACCGAGTT | GCTCTTGCCC | GGCGTCAATA | CGGGATAATA | CCGCGCCACA 6540 |
| TAGCAGAACT | TTAAAAGTGC | TCATCATTGG | AAAACGTTCT | TCGGGGCGAA | AACTCTCAAG 6600 |
| GATCTTACCG | CTGTTGAGAT | CCAGTTCGAT | GTAACCCACT | CGTGCACCCA | ACTGATCTTC 6660 |
| AGCATCTTTT | ACTTTCACCA | GCGTTTCTGG | GTGAGCAAAA | ACAGGAAGGC | AAAATGCCGC 6720 |
| AAAAAAGGGA | ATAAGGGCGA | CACGGAAATG | TTGAATACTC | ATACTCTTCC | TTTTTCAATA 6780 |
| TTATTGAAGC | ATTTATCAGG | GTTATTGTCT | CATGAGCGGA | TACATATTTG | AATGTATTTA 6840 |
| GAAAAATAAA | CAAATAGGGG | TTCCGCGCAC | ATTTCCCCGA | AAAGTGCCAC | CTGACG 6896 |

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | |
|---|---|---|---|
| GATCGGATCC | ATGGACCACC | TCGGGGCGTC | CCTC 34 |

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | |
|---|---|---|---|
| AGCTTCGAGC | GGCCGCGGGG | TCCAGGTCGC | TAGGCGTCAG 40 |

( 2 ) INFORMATION FOR SEQ ID NO:9:

( i ) SEQUENCE CHARACTERISTICS:
        ( A ) LENGTH: 750 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

| | | | | | |
|---|---|---|---|---|---|
| ATGGACCACC | TCGGGGCGTC | CCTCTGGCCC | CAGGTCGGCT | CCCTTTGTCT | CCTGCTCGCT 60 |
| GGGGCCGCCT | GGGCGCCCCC | GCCTAACCTC | CCGGACCCCA | AGTTCGAGAG | CAAAGCGGCC 120 |
| TTGCTGGCGG | CCCGGGGGCC | CGAAGAGCTT | CTGTGCTTCA | CCGAGCGGTT | GGAGGACTTG 180 |
| GTGTGTTTCT | GGGAGGAAGC | GGCGAGCGCT | GGGGTGGGCC | CGGGCAACTA | CAGCTTCTCC 240 |
| TACCAGCTCG | AGGATGAGCC | ATGGAAGCTG | TGTCGCCTGC | ACCAGGCTCC | CACGGCTCGT 300 |
| GGTGCGGTGC | GCTTCTGGTG | TTCGCTGCCT | ACAGCCGACA | CGTCGAGCTT | CGTGCCCCTA 360 |
| GAGTTGCGCG | TCACAGCAGC | CTCCGGCGCT | CCGCGATATC | ACCGTGTCAT | CCACATCAAT 420 |
| GAAGTAGTGC | TCCTAGACGC | CCCCGTGGGG | CTGGTGGCGC | GGTTGGCTGA | CGAGAGCGGC 480 |
| CACGTAGTGT | TGCGCTGGCT | CCCGCCGCCT | GAGACACCCA | TGACGTCTCA | CATCCGCTAC 540 |
| GAGGTGGACG | TCTCGGCCGG | CAACGGCGCA | GGGAGCGTAC | AGAGGGTGGA | GATCCTGGAG 600 |
| GGCCGCACCG | AGTGTGTGCT | GAGCAACCTG | CGGGGCCGGA | CGCGCTACAC | CTTCGCCGTC 660 |
| CGCGCGCGTA | TGGCTGAGCC | GAGCTTCGGC | GGCTTCTGGA | GCGCCTGGTC | GGAGCCTGTG 720 |

TCGCTGCTGA CGCCTAGCGA CCTGGACCCC                                          750

( 2 ) INFORMATION FOR SEQ ID NO:10:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

GATCGGATCC ATGGGGTGGC TTTGCTCTGG GCTC                                      34

( 2 ) INFORMATION FOR SEQ ID NO:11:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

AGCTTCGAGC GGCCGCGTGC TGCTCGAAGG GCTCCCTGTA                                40

( 2 ) INFORMATION FOR SEQ ID NO:12:

( i ) SEQUENCE CHARACTERISTICS:
    ( A ) LENGTH: 686 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

ATGGGGTGGC TTTGCTCTGG GCTCCTGTTC CCTGTGAGCT GCCTGGTCCT GCTGCAGGTG           60
GCAAGCTCTG GGAACATGAA GGTCTTGCAG GAGCCCACCT GCGTCTCCGA CTACATGAGC          120
ATCTCTACTT GCGAGTGGAA GATGAATGGT CCCACCAATT GCAGCACCGA GCTCCGCCTG          180
TTGTACCAGC TGGTTTTTCT GCTCTCCGAA GCCCACACGT GTATCCCTGA GGCGCGGGGT          240
GCGTGTGCCA CCTGCTCATG GATGACGTGG TCAGTGCGGA TAACTATACA CTGGACCTGT          300
GGGCTGGGCA GCAGCTGCTG TGGAAGGGCT CCTTCAAGCC CAGCGAGCAT GTGAAACCCA          360
GGGCCCCAGG AAACCTGACA GTTCACACCA ATGTCTCCGA CACTCTGCTG CTGACCTGGA          420
GCAACCCGTA TCCCCCTGAC AATTACCTGT ATAATCATCT CACCTATGCA GTCAACATTT          480
GGAGTGAAAA CGACCCGGCA GATTTCAGAA TCTATAACGT GACCTACCTA GAACCCTCCC          540
TCCGCATCGC AGCCAGCACC CTGAAGTCTG GGATTCCTA CAGGGCACGG GTGAGGGCCT           600
GGGCTCAGTG CTATAACACC ACCTGGAGTG AGTGGAGCCC CAGCACCAAG TGGCACAACT          660
CCTACAGGGA GCCCTTCGAG CAGCAC                                              686

( 2 ) INFORMATION FOR SEQ ID NO:13:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GATCGAATTC ATGCTGGCCG TCGGCTGCGC GCTG                                      34

( 2 ) INFORMATION FOR SEQ ID NO:14:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:14:

| | | | | |
|---|---|---|---|---|
| AGCTTCGAGC | GGCCGCATCT | TGCACTGGGA | GGCTTGTCGC | 40 |

( 2 ) INFORMATION FOR SEQ ID NO:15:

( i ) SEQUENCE CHARACTERISTICS:
    ( A ) LENGTH: 1074 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

| | | | | | |
|---|---|---|---|---|---|
| ATGCTGGCCG | TCGGCTGCGC | GCTGCTGGCT | GCCCTGCTGG | CCGCGCCGGG | AGCGGCGCTG | 60
| GCCCCAAGGC | GCTGCCCTGC | GCAGGAGGTG | GCAAGAGGCG | TGCTGACCAG | TCTGCCAGGA | 120
| GACAGCGTGA | CTCTGACCTG | CCCGGGGGTA | GAGCCGGAAG | ACAATGCCAC | TGTTCACTGG | 180
| GTGCTCAGGA | AGCCGGCTGC | AGGCTCCCAC | CCCAGCAGAT | GGGCTGGCAT | GGGAAGGAGG | 240
| CTGCTGCTGA | GGTCGGTGCA | GCTCCACGAC | TCTGGAAACT | ATTCATGCTA | CCGGGCCGGC | 300
| CGCCCAGCTG | GGACTGTGCA | CTTGCTGGTG | GATGTTCCCC | CCGAGGAGCC | CCAGCTCTCC | 360
| TGCTTCCGGA | AGAGCCCCCT | CAGCAATGTT | GTTTGTGAGT | GGGGTCCTCG | GAGCACCCCA | 420
| TCCCTGACGA | CAAAGGCTGT | GCTCTTGGTG | AGGAAGTTTC | AGAACAGTCC | GGCCGAAGAC | 480
| TTCCAGGAGC | CGTGCCAGTA | TTCCCAGGAG | TCCCAGAAGT | TCTCCTGCCA | GTTAGCAGTC | 540
| CCGGAGGGAG | ACAGCTCTTT | CTACATAGTG | TCCATGTGCG | TCGCCAGTAG | TGTCGGGAGC | 600
| AAGTTCAGCA | AAACTCAAAC | CTTTCAGGGT | TGTGGAATCT | TGCAGCCTGA | TCCGCCTGCC | 660
| AACATCACAG | TCACTGCCGT | GGCCAGAAAC | CCCCGCTGGC | TCAGTGTCAC | CTGGCAAGAC | 720
| CCCCACTCCT | GGAACTCATC | TTTCTACAGA | CTACGGTTTG | AGCTCAGATA | TCGGGCTGAA | 780
| CGGTCAAAGA | CATTCACAAC | ATGGATGGTC | AAGGACCTCC | AGCATCACTG | TGTCATCCAC | 840
| GACGCCTGGA | GCGGCCTGAG | GCACGTGGTG | CAGCTTCGTG | CCCAGGAGGA | GTTCGGGCAA | 900
| GGCGAGTGGA | GCGAGTGGAG | CCCGGAGGCC | ATGGGCACGC | CTTGGACAGA | ATCCAGGAGT | 960
| CCTCCAGCTG | AGAACGAGGT | GTCCACCCCC | ATGCAGGCAC | TTACTACTAA | TAAAGACGAT | 1020
| GATAATATTC | TCTTCAGAGA | TTCTGCAAAT | GCGACAAGCC | TCCCAGTGCA | AGAT | 1074

( 2 ) INFORMATION FOR SEQ ID NO:16:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

| | | | |
|---|---|---|---|
| GATCGGATCC | ATGCTGGGCA | TCTGGACCCT | CCTACC | 36

( 2 ) INFORMATION FOR SEQ ID NO:17:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

-continued

AGCTTCGAGC GGCCGCGTTA GATCTGGATC CTTCCTCTTT GC            42

( 2 ) INFORMATION FOR SEQ ID NO:18:

( i ) SEQUENCE CHARACTERISTICS:
        ( A ) LENGTH: 509 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

ATGCTGGGCA TCTGGACCCT CCTACCTCTG GTTCTTACGT CTGTTGCTAG ATTATCGTCC            60

AAAAGTGTTA ATGCCCAAGT GACTGACATC AACTCCAAGG GATTGGAATT GAGGAAGACT            120

GTTACTACAG TTGAGACTCA GAACTTGGAA GGCCTGCATC ATGATGGCCA ATTCTGCCAT            180

AAGCCCTGTC CTCCAGGTGA AAGGAAAGCT AGGGACTGCA CAGTCAATGG GGATGAACCA            240

GACTGCGTGC CCTGCCAAGA AGGGAAGGAG TACACAGACA AAGCCCATTT TTCTTCCAAA            300

TGCAGAAGAT GTAGATTGTG TGATGAAGGA CATGGCTTAG AAGTGGAAAT AAACTGCACC            360

CGGACCCAGA ATACCAAGTG CAGATGTAAA CCAAACTTTT TTTGTAACTC TACTGTATGT            420

GAACACTGTG ACCCTTGCAC CAAATGTGAA CATGGAATCA TCAAGGAATG AGCAACACCA            480

AGTGCAAAGA GGAAGGATCC AGATCTAAC                                             509

( 2 ) INFORMATION FOR SEQ ID NO:19:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GCCRCCATGG            10

COMPOSITIONS AND METHODS FOR SCREENING DRUG LIBRARIES

FIELD OF THE INVENTION

The present invention relates to the fields of chemistry, molecular biology and biochemistry. The invention relates to methods for identifying, from a large collection of random or non-random synthetic molecules, candidates of such molecules able to bind a specific domain of a target molecule. The invention therefore has useful applications in fields including basic biochemical and biomedical research and drug development.

BACKGROUND OF THE INVENTION

A significant recent development in pharmaceutical drug discovery and design has been the development of combinatorial chemistry to create chemical libraries of potential new drugs. Chemical libraries are intentionally created collections of different molecules; these molecules can be made by organic synthetic methods or biochemically. In the latter case, the molecules can be made in vitro or in vivo.

Combinatorial chemistry is a synthetic strategy in which the chemical members of the library are made according to a systematic methodology by the assembly of chemical subunits. Each molecule in the library is thus made up of one or more of these subunits. The chemical subunits may include naturally-occurring or modified amino acids, naturally-occurring or modified nucleotides, naturally-occurring or modified saccharides or other molecules, whether organic or inorganic. Typically, each subunit has at least two reactive groups, permitting the stepwise construction of larger molecules by reacting first one then another reactive group of each subunit to build successively more complex and potentially diverse molecules.

By creating synthetic conditions whereby a fixed number of individual building blocks, for example, the twenty naturally-occurring amino acids, are made equally available at each step of the synthesis, a very large array or library of compounds can be assembled after even a few steps of the synthesis reaction. Using amino acids as an example, at the first synthetic step the number of resulting compounds (N) is equal to the number of available building blocks, designated as b. In the case of the naturally-occurring amino acids, b=20. In the second step of the synthesis, assuming that each amino acid has an equal opportunity to form a dipeptide with every other amino acid, the number of possible compounds $N=b^2=20^2=400$.

For successive steps of the synthesis, again assuming random, equally efficient assembly of the building blocks to the resulting compounds of the previous step, $N=b^x$ where x equals the number of synthetic assembly steps. Thus it can be seen that for random assembly of only a decapeptide the number of different compounds is $20^{10}$ or $1.02\times10^{13}$. Such an extremely large number of different compounds permits the assembly and screening of a large number of diverse candidates for a desired enzymatic, immunological or biological activity.

Biologically synthesized combinatorial libraries have been constructed using techniques of molecular biology in bacteria or bacteriophage particles. For example, U.S. Pat. No. 5,270,170 and 5,338,665 to Schatz describe the construction of a recombinant plasmid encoding a fusion protein created through the use of random oligonucleotides inserted into a cloning site of the plasmid. This cloning site is placed within the coding region of a gene encoding a DNA binding protein, such as the lac repressor, so that the specific binding function of the DNA binding protein is not destroyed upon expression of the gene. The plasmid also contains a nucleotide sequence recognized as a binding site by the DNA binding protein. Thus, upon transformation of a suitable bacterial cell and expression of the fusion protein, the protein will bind the plasmid which produced it. The bacterial cells are then lysed and the fusion proteins assayed for a given biological activity. Moreover, each fusion protein remains associated with the nucleic acid which encoded it; thus through nucleic acid amplification and sequencing of the nucleic acid portion of the protein:plasmid complexes which are selected for further characterization, the precise structure of the candidate compound can be determined. The Schatz patents are incorporated herein by reference.

In other biological systems, for example as described in Goedell et al., U.S. Pat. No. 5,223,408, nucleic acid vectors are used wherein a random oligonucleotide is fused to a portion of a gene encoding the transmembrane portion of an integral protein. Upon expression of the fusion protein it is embedded in the outer cell membrane with the random polypeptide portion of the protein facing outward. Thus, in this sort of combinatorial library the compound to be tested is linked to a solid support, i.e., the cell itself. A collection of many different random polypeptides expressed in this way is termed a display library because the cell which produced the protein "displays" the drug on its surface. Since the cell also contains the recombinant vector encoding the random portion of the fusion protein, cells bearing random polypeptides which appear promising in a preliminary screen can be lysed and their vectors extracted for nucleic acid sequencing, deduction of the amino acid sequence of the random portion of the fusion protein, and further study. The Goedell patent is incorporated herein by reference.

Similarly, bacteriophage display libraries have been constructed through cloning random oligonucleotides within a portion of a gene encoding one or more of the phage coat proteins. Upon assembly of the phage particles, the random polypeptides also face outward for screening. As in the previously described system, the phage particles contain the nucleic acid encoding the fusion protein, so that nucleotide sequence information identifying the drug candidate is linked to the drug itself. Such phage expression libraries are described in, for example, Sawyer et al., 4 *Protein Engineering* 947–53 (1991); Akamatsu et al., 151 *J. Immunol.* 4651–59 (1993), and Dower et al., U.S. Pat. No. 5,427,908. These patents and publications are incorporated herein by reference.

While synthesis of combinatorial libraries in living cells has distinct advantages, including the linkage of the compound to be tested with a nucleic acid capable of amplification by the polymerase chain reaction or another nucleic acid amplification method, there are clear disadvantages to using such systems as well. The diversity of a combinatorial library is limited by the number and nature of the building blocks used to construct it; thus modified or R-amino acids or atypical nucleotides may not be able to be used by living cells (or by bacteriophage or virus particles) to synthesize novel peptides and oligonucleotides. There is also a limiting selective process at play in such systems, since compounds having lethal or deleterious activities on the host cell or on bacteriophage infectivity or assembly processes will not be present or may be negatively selected for in the library. Importantly, only peptide or oligonucleotide compounds are made in such systems; thus the diversity of the library is restricted to peptide and polynucleotide macromolecules composed of naturally-occurring monomeric units.

Other approaches to creating molecularly diverse combinatorial libraries employ chemical synthetic methods to make use of atypical or non-biological building blocks in the assembly of the compounds to be tested. Thus, Zuckermann et al., 37 *J. Med. Chem.* 2678–85 (1994), describe the construction of a library using a variety of N-(substituted) glycines for the synthesis of peptide-like compounds termed "peptoids". The substitutions were chosen to provide a series of aromatic substitutions, a series of hydroxylated side substitutions, and a diverse set of substitutions including branched, amino, and heterocyclic structures. This publication is incorporated by reference herein.

Other workers have used small bi- or multifunctional organic compounds instead of, or in addition to, amino acids for the assembly of libraries or collections compounds of medical or biological interest.

Using chemical synthetic methodologies to create large diverse libraries of potentially useful compounds permits the synthesis of compounds joined to a solid support of some kind. However, the use of such synthetic methods requires the ability, after synthesis, to identify the structure of the rare members of the library which are able to pass a screening process. Thus, such libraries must be rationally designed so as to permit such identification. This task becomes virtually overwhelming as the number of possible compounds grows multiplicatively.

In attempting to consider this latter point, a number of attempts have been made to devise post-screening methods of "addressing" the specific compounds that the screening process indicates as candidates for further study. One class of such addressable libraries employs a strategy of linking the individual peptides of the library with the nucleic acids encoding them. Examples of such systems, such as the use of biological entities such as bacteriophage displaying the compounds of the library or plasmid-binding proteins fused to member compounds of the library have been described above. However, this methodology is not limited to biological systems, and can be employed by the co-polymerization of the test compound and a corresponding nucleotide sequence onto a single solid support.

Another strategy involves chemically synthesizing the combinatorial libraries on solid supports in a methodical and predetermined fashion, so that the placement of each library member gives information concerning the synthetic structure of that compound. Examples of such methods are described, for example, in Geysen, U.S. Pat. No. 4,833,092, in which compounds are synthesized on functionalized polyethylene pins designed to fit a 96 well microtiter dish so that the position of the pin gives the researcher information as to the compound's structure. Similarly Hudson et al., PCT Publication No. WO94/05394, describe methods for the construction of combinatorial libraries of biopolymers, such as polypeptides, oligonucleotides and oligosaccharides, on a spatially addressable solid phase plate coated with a functionalized polymer film. In this system the compounds are synthesized and screened directly on the plate. Knowledge of the position of a given compound on the plate yields information concerning the nature and order of building blocks comprising the compound. Similar methods of constructing addressable combinatorial libraries may be used for the synthesis of compounds other than biopolymers.

Another approach has been the use of large numbers of very small derivatized beads, which are divided into as many equal portions as there are different building blocks. In the first step of the synthesis, each of these portions is reacted with a different building block. The beads are then thoroughly mixed and again divided into the same number of equal portions. In the second step of the synthesis each portion, now theoretically containing equal amounts of each building block linked to a bead, is reacted with a different building block. The beads are again mixed and separated, and the process is repeated as desired to yield a large number of different compounds, with each bead containing only one type of compound.

This methodology, termed the "one-bead one-compound" method, yields a mixture of beads with each bead potentially bearing a different compound. Thus, in this method the beads themselves cannot be considered "addressable" in the same sense as in the solid phase supports and arrays described above, or as in the cellular or phage libraries. However, the compounds displayed in the surface of each bead can be tested for the ability to bind with a specific compound, and, if those (typically) few beads are able to be identified and separated from the other beads, a presumable pure population of compounds can be recovered and analyzed. Of course, this latter possibility depends upon the ability to load and extract enough information concerning the compounds on the surface of each bead to be susceptible to meaningful subsequent analysis. Such information may simply be in the form of an adequate amount of the compound of interest to be able to determine its structure. For example, in the case of a peptide, enough of the peptide must be synthesized on the bead to be able to perform peptide sequencing and obtain the amino acid sequence of the peptide.

For synthetic chemical libraries, not limited to the one-bead one-compound method, in which the compounds of interest are not naturally-occurring peptides or oligonucleotides, analysis can be a tedious and difficult undertaking. In these cases, a code made from easily synthesized and analyzed "tag" molecules (for example, amino acids or other small multifunctional molecules, such as halogenated aromatics) can be co-synthesized with the compounds comprising the library. After a screening procedure, the tag can be "uncoded" to elucidate the structure of the compounds of interest. The code can be relatively arbitrary, so that the structure of any test compound made of building blocks, in which the building block members are able to be designated as corresponding, for example, to an amino acid (or dipeptide, tripeptide etc.), can be determined in this way.

As described above, the construction of combinatorial libraries provides researchers the opportunity to construct a vast number of potential chemical candidates to answer basic and applied structure-function questions, such as, without limitation: the relationship between a ligand and its receptor, a given antibody and its antigen and an enzyme and substrate. However, the ability to generate large libraries of potential drug compounds overwhelms most available screening methods. Thus, a bottleneck of this emerging and powerful technology remains adequate high-throughput screening procedures to identify the few compounds which are potential candidates for further study from among the thousands, millions or billions of other compounds in the library.

When the combinatorial library is to be screened for the presence of therapeutic or diagnostic agents, candidate compounds are generally initially screened for their ability to bind to a particular member of biological binding partners. By "binding partners" is meant that two or more compounds are able to join under appropriate biological or in vitro conditions to form a specific complex. Examples of such binding partners are, without limitation, antibody and antigen, ligand and receptor, and enzyme and substrate. At times, either ligand or receptor, or both may be comprised of a complex of more than one compound or polypeptide chain. For example, in the case of tumor necrosis factor α (TNFα), the soluble ligand TNF appears to bind to its receptor in the form of a TNF homotrimer; each TNF trimer can bind three copies of the receptor and clustering of the TNF receptor is thought to be required for it to exert its biological effects. Each and all polypeptide chains involved in the binding of the TNF trimer to the clustered receptors are considered individual binding partners.

One common screening method currently applied consists of coating a solid support, such as the wells of a microtiter dish, with the specific molecule for which a binding partner is sought. The library member compounds are then labeled, plated onto the solid support, and allowed to bind the library members. After a wash step, the binding partner complexes are then detected by detection of the label joined to the bound library members. This type of procedure is particularly well suited to combinatorial libraries wherein the member compounds are provided in a solution or medium. This method can be somewhat labor intensive and, in order to achieve the high throughput required to screen such large numbers of test compounds, may as a first step require screening pools of test compounds, followed by one or more rescreening step in order to specifically identify the compound of interest. The situation can also be reversed, so that the library members are allowed to coat individual wells and are probed with the specific molecule.

In cases wherein the combinatorial library is to contain antibody analogs or peptides targeted to a given epitope, the library members may contain a portion of an antibody recognized by a secondary antibody able to be detected, for example in an enzyme-linked immunological assay (ELISA) or by virtue of being directly or indirectly labeled, for example with a radionuclide, a chemiluminescent compound, a fluor, and enzyme or dye.

Tawfik et al., 90 *Proc. Natl. Acad. Sci.* 373–77 (1993) describe a method of screening a library of antibodies (in this case, from a hybridoma library generated using a mimic of the transition state intermediate of an enzymatic reaction) for the presence of rare antibodies having a desired catalytic activity. The screening compound, in this case the enzyme substrate, was immobilized on 96 well microtiter dishes. Supernatants from each clone were placed into separate wells under conditions promoting the enzymatic reaction. The products of the enzymatic reaction, still immobilized to the microtiter dish, were assayed by the use of product-specific monoclonal antibodies. Again, this type of screening process is quite labor-intensive and may necessitate repetitive screening of pools of test compounds in order to achieve high throughput of large libraries.

In the cellular or phage display libraries and "one-bead one-compound" synthetic libraries described above the library members can be screened for the ability to bind a specific binding partner (e.g., a receptor) which is labeled with a detectable fluor, such as fluorescein or phycoerythrin. Because each particle (for example, a cell or a bead) displays only one species of test compound, the fluorescently labeled particles can be detected and sorted using a fluorescence activated cell sorter (FACS). An enriched population of positive beads or particles can then be rescreened, if necessary, and individually analyzed. This strategy can be employed using cells displaying the test compounds or beads on which the test compounds are synthesized. However, this method also suffers from a lack of ease of use, and is time intensive.

Whether screening is by the panning procedure previously described or by binding of labels to the solid phase bound test compounds, a common screening procedure is by competitive binding of the test compounds in the presence of a detectable control ligand, often the natural ligand for the specific binding partner to which the test compounds are intended to be directed. Again, this method can be quite labor-intensive and requires the generation of a standard curve and correlation of the data obtained from the competition experiments with the standard curve in order to generate meaningful data. Thus, competition assays are unable to yield easily interpreted and rapid results in an initial screen of thousands or millions of different library members.

ELISA and similar assay formats are useful when the library members are derivatives of antibodies and contain variable regions directed against known antigens. However, these methods may not be as useful in a non-competitive (i.e., direct) format where neither the specific binding partner nor the desired test compounds are antibodies or contain an available epitope against which a secondary antibody can be easily generated.

Biochemical tools have been generated consisting of chimeric peptides containing portions of a peptide ligand and specific domains of an antibody. Such agents have been devised mainly as therapeutic aids to the delivery of drugs within a patient's body. Especially in the case of peptide drugs, such as soluble agonists of cytokines and other such agents, therapeutic agents or drugs often have a short systemic half-life which reduces the stability of such drugs in vivo. This reduced stability may, in some cases, be counteracted by higher or more frequent dosages, but this may lead to such undesirable consequences as drug tolerance, toxic effects, and high cost of the drug to the patient.

One strategy for overcoming these shortcomings, particularly with regard to the use of systemic biochemical angonists, has been the use of fusion peptides, which have a longer half life in the circulatory system. These fusion peptides generally contain a binding partner, such as a cytokine receptor, fused to part of an immunoglobulin chain. The immunoglobulin chain acts as molecular camouflage, reducing the opportunity for the binding partner to be recognized as a "foreign" antigen by the organism.

Thus, Shin, et al., 92 *Proc Nat'l Acad. Sci.* 2820–24 (1995) employed fusion peptides made by constructing recombinant vectors having the gene encoding human transferrin fused, in frame, to the 3' end of a chimeric mouse-human IgG3 gene encoding variable and constant regions. The resulting fusion molecules were able to bind antigen (dansyl) and the purified transferrin receptor, and were able to enter the brain parenchyma of rats using the transferrin receptor for transport from the circulatory system. The remaining variable region of the antibody could contain other optional specificities, thus the site is available for secondary targeting of the molecule, such as for therapeutic purposes, once across the blood-brain barrier.

Evans and coworkers, 180 *J. Exp. Med.* 2173–79 (1994), using molecular cloning techniques, reported the construction of a fusion protein containing extracellular portions of the p75 high affinity receptor or, alternatively the p55 low affinity receptor, specific for tissue necrosis factor alpha (TNFα-R) fused to a constant region of human IgG. The soluble, non-fusion forms of the TNF receptors are known to be rapidly degraded in vivo. Cells were transformed with vectors expressing portions of heavy immunoglobulin chain fused to each of TNF receptors. The fusion peptide was more stable than the soluble receptor in serum. Moreover, the fusion peptides were secreted as dimers containing two heavy chains bound by disulfide linkages. The dimers were able to bind the TNF trimers (a naturally-occurring conformation of TNFα) in two separate areas and thus with higher affinity than is possible when the fusion peptide is in the soluble monomeric form.

Other fusion proteins containing a ligand or receptor and an antibody portion have been used in the search for effective therapeutic agonists to humoral agents. In Fountoulakis et al., 270 *J. Biol. Chem.* 3958–64 (1995) the extracellular domain of the human interferon γ receptor was expressed as a fusion protein with the IgG hinge, $C_H2$ and $C_H3$ domains, and was shown to bind interferon, compete for interferon binding to the cell surface receptor of tissue culture cells, and inhibit interferon-mediated antiviral activity. Due to the immunoglobulin portion of the fusion protein, the protein was expressed in Chinese Hamster ovary cells as a disulfide-linked homodimer. The dimer was able to bind interferon more strongly than the soluble receptor monomer.

In Pitti, et al., 31 Molec. *Immunol.* 1345–51 (1994) the human interleukin-1 (IL-1) receptor was expressed in transfected human cells as a fusion protein containing the hinge and Fc regions of the IgG heavy chain. This fusion peptide was reported to have an extended pharmacological half-life in the circulatory system of mice and to bind IL-1.

Crowe et al., 168 *J. Immunol. Meth.* 79–89 (1994) expressed a gene containing coding sequences of the extracellular domain of the human lymphotoxin a receptor fused to a gene segment encoding the constant portion of human IgG heavy chain. The fusion protein was cloned into a baculovirus vector and expressed in both insect cells and African green monkey kidney cells as a dimer. The IgG portion of the fusion peptide was used as a ligand for affinity purification of the fusion peptide, and also enabled disulfude facilitated dimerization of the fusion peptides to provide a high-affinity ligand for lymphotoxin.

These latter five references are incorporated by reference herein.

SUMMARY OF THE INVENTION

The present invention is directed to a method of screening candidate biologically active molecules, preferably, though not necessarily contained in combinatorial chemical libraries, in which a multifunctional chimeric protein is constructed and used to directly bind candidate compounds in a screening process for biological activity or binding avidity. The chimeric protein contains at least a portion of a specific binding partner or a peptide analog thereof, with which test compounds are sought to interact. Preferably, the specific binding partner is a ligand or ligand receptor. The chimeric protein also contains at least one portion of an antibody chain which is able to recognize an antigen, able to be recognized as an epitope, and/or which functions as an immunoglobulin hinge domain. In a particularly preferred embodiment the chimeric protein contains an immunoglobulin domain which is able to recognize an antigen and/or able to be recognized as an epitope and also contains the flexible "hinge" region of the immunoglobulin heavy chain placed at a location between the immunoglobulin portion of the chimeric protein and the receptor moiety. Preferably, the immunoglobulin portion of the chimeric protein is derived from an immunoglobulin heavy chain.

DETAILED DESCRIPTION OF THE INVENTION

Definitions

By "specific molecule" is meant a molecule such as, without limitation, a ligand; a receptor, such as a cell surface receptor able to bind a ligand; an antibody; an antigen; an enzyme; a hormone; and an enzyme substrate. As will be clear from the specification, the chimeric protein used in the methods of the present invention need not contain all of a specific molecule or its peptide analog, but need only contain enough of a portion to be recognized and bound by a given compound. A specific molecule need not be naturally occurring; it only need be a molecule for whom one or more binding partner is sought to be found.

By "peptide analog" is meant a molecule or part thereof which is comprised of amino acids and resembles, with regard to its binding ability and/or specificity, a specific molecule, as defined above. Such peptide analogs may be found or constructed by protein engineering techniques, such methods being well known to those of skill in the art. Alternatively, such peptide analogs may be found by a reiterative screening process, for example wherein a natural binding partner of the specific molecule (which specific molecule is not necessarily a protein or peptide), or a portion thereof, is used as described herein (i.e. in a chimeric protein) to screen peptide compounds for the ability to bind to it. In a second screening step, the newly found peptide compound (or a portion thereof) may itself be used as a peptide analog of the specific molecule in a chimeric protein to screen for analogs of the natural binding partner. Other methods for finding or making peptide analogs will be apparent to those of skill in the art.

By "epitope" is meant an antigen or portion thereof which is capable of binding with an antibody as an antigenic determinant.

By "binding partner complex" is meant the association of two or more molecules which are bound to each other in a specific, detectable manner; thus the association of ligand and receptor, antibody and antigen, and chimeric protein and the compound to which it binds.

By "chimeric protein" is meant a non naturally-occuring protein or polypeptide comprising some or all of the amino acid sequences from at least two different proteins or polypeptides, or of one protein or polypeptide and a non naturally occuring polypeptide chain. As used herein, a chimeric protein is designed, made, or selected intentionally, and contains at least two domains.

By "directly or indirectly labeled" is meant that a molecule may contain a label moiety which moiety emits a signal which is capable of being detected, such as a radioisotope, a dye, or a fluorescent or chemiluminescent moiety, or may contain a moiety, such as an attached enzyme, ligand such as biotin, enzyme substrate, epitope, or nucleotide sequence which is not itself detected but which, through some additional reaction, is capable of indicating the presence of the compound.

By "secondary molecule" is meant a molecule which is able to bind to a region within the second domain of the chimeric protein, thereby allowing its detection or purification.

By "hinge region" or "immunoglobulin heavy chain hinge region" is meant one of a family of proline and cysteine-containing amino acid sequence regions which occur between the $C_H2$ and $C_H1$ regions of many immunoglobulin heavy chains, or analogs of these amino acid sequences based thereon, in which the regions to the amino and carboxy terminal side of the hinge are spacially separated by a turn or kink in the polypeptide chain so as to facilitate their separate and simultaneous specific binding with other molecules.

By "ligand" is meant a molecule or a multimeric molecular complex which is able to specifically bind another given molecule or molecular complex. Often, though not necessarily, a ligand is soluble while its target is immobilized, such as by an anchor domain imbedded into a cell membrane.

By "receptor" is meant at least a portion of a molecule, or a multimeric molecular complex which has an anchor domain embedded into a cell membrane and is able to bind a given molecule or molecular complex. Many receptors have particularly high affinity for a ligand when either or both the receptor or ligand are in a homo- or hetero multimeric form, such as a dimer.

By "solid support" is meant an insoluble matrix either biological in nature, such as, without limitation, a cell or bacteriophage particle, or synthetic, such as, without limitation, an acrylamide derivative, cellulose, nylon, silica, and magnetized particles, to which soluble molecules may be linked or joined.

By "naturally-occuring" is meant normally found in nature. Although a chemical entity may be naturally occurring in general, it need not be made or derived from natural sources in any specific instance.

By "non naturally-occurring" is meant rarely or never found in nature and/or made using organic synthetic methods.

By "bivalent" is meant able to specifically bind two chemical compounds.

By "multivalent" is meant able to specifically bind two or more chemical compounds.

By "bifunctional" means a compound having two distinct chemical groups capable of separate reaction with one or more additional compound.

By "multifunctional" is meant a compound having two or more distinct chemical groups capable of separate reaction with one or more additional compound.

By "multimeric complex" is meant the stable covalent or non-covalent association of two or more identical or different polypetide chains to form a structure capable of recognition by a binding partner.

By "modified" is meant non naturally-occuring or altered in a way that deveates from naturally-occurring compounds.

The chimeric protein of the instant invention is useful as a tool in screening a population of compounds for the ability to bind a specific binding partner, at least a portion of said specific binding partner, or a protein or peptide analog thereof, which is comprised in a first binding domain of the chimeric protein. In preferred embodiments the same chimeric molecule also contains a second binding domain comprising at least one immunologically active region (antigenic or antigen-binding) which confers one or more additional binding specificity. This additional specificity may be used as a means for detecting the chimeric protein; for example and without limitation, through the use of a directly or indirectly labeled secondary antibody, or as means for the binding and/or affinity purification of the chimeric protein or compound of interest using, for example, immobilized Protein A or Protein G or an immobilized antibody able to bind the second domain of the chimeric protein. If the second binding domain of the chimeric protein is not derived from an immunoglobulin chain, it may simply comprise a chain of amino acids to which is bound a ligand such as avidin or biotin; however, in such a case the chimeric protein will contain at least a proline-containing hinge region derived from an immunoglobulin chain.

While the method of the present invention is particularly useful as a tool for the screening of combinatorial library members, it may be used to screen bacterial or phage lysates, or in any diagnostic or analytical assay or preparative protocol in which a specific interaction between binding partners is sought to be detected or a compound is sought to be isolated.

Examples of biochemicals known or thought to exert biological effects by way of specific or semispecific binding to a receptor or binding partner include the following: growth hormone, human growth hormone, bovine growth hormone, parathyroid hormone, thyroxine, insulin A-chain, insulin-B chain, proinsulin, relaxin A-chain, leptin receptor, fibroblast growth factor, relaxin B-chain, prorelaxin, follicle stimulating hormone, thyroid stimulating hormone, luteinizing hormone, glycoprotein hormone receptors, calcitonin, glucagon, factor VIII, an antibody, lung surfactant, urokinase, streptokinase, tissue plasminogen activator, bombesin, factor IX, thrombin, hemopoietic growth factor, tumor necrosis factor alpha, tumor necrosis factor beta, enkephalinase human serum albumin, mullerian-inhibiting substance, gonadotropin-associated peptide, $\beta$ lactamase, tissue factor protein, inhibitin, activin, vascular endothelial growth factor, integrin receptors, thrombopoietin, protein A or D, rheumatoid factors, NGF-$\beta$, platelet growth factor, transforming growth factor, TGF-$\alpha$, TGF -$\beta$, insulin-like growth factor I and II, insulin growth factor binding proteins, CD4, CD8, Dnase, Rnase, latency associated peptide, erythropoietin, osteoinductive factors, interferon-alpha, -beta and -gamma, colony stimulating factors, M-CSF, GM-CSF, G-CSF, stem cell factor, interleukins, IL-1, IL-2, IL-3, IL-4, IL-5, IL-6, IL-7, IL-8, IL-9, IL-10, IL-11, IL-12, superoxide dismutase, viral antigens, HIV envelope proteins, gp120, gp140, immunoglobulins, and proteins encoded by the Ig supergene family. These proteins, their ligands or receptors, and fragments or portions of these are included as among potential binding partners contained in the first domain of the chimeric protein.

Thus, in one aspect, the present invention is directed to methods for detecting or isolating a compound comprising contacting the compound with a chimeric protein which contains a first domain comprising a specific binding partner, such as at least a portion of a receptor, antigen, antibody, ligand, enzyme, enzyme substrate or other protein as mentioned above, and a second domain comprising at least one region of an immunoglobulin molecule which is able to specifically bind with an antigen or an antibody, wherein the molecule recognized by the first domain is different than the molecule recognized by the second domain. Preferably, the first domain and the second domain are separated by the proline-containing "hinge" region of an immunoglobulin heavy chain so as to sterically separate the two domains. The chimeric protein is also preferably, though not necessarily, expressed from a vector-borne recombinant DNA molecule containing a nucleotide sequence encoding the chimeric protein. The first domain may be situated either to the amino terminal side or the carboxy terminal side of the second domain; in a particularly preferred embodiment the chimeric protein has the first domain situated to the amino terminal side of the second domain.

In this aspect of the invention the compound of interest, if present, will bind to a region within the first domain of the chimeric protein. If the compound is immobilized, such as in a cellular or phage display library or in the "one-bead, one-compound" libraries, the solid support can then be washed free of excess chimeric protein and the chimeric protein:compound conjugate (binding partner complex)

detected. In a preferred embodiment, the chimeric protein is detected by binding the second domain of the chimeric protein with a labeled secondary binding partner, such as a enzyme-labeled anti-IgG secondary antibody, specific for a region of the second domain. Detection of the secondary antibody permits identification of solid supports containing compounds which are able to interact with the binding partner of the first domain. These compounds can then be analyzed for elucidation of their structure or in additional assay protocols.

In this preferred embodiment, if the labeled secondary binding partner used to bind the second domain has a fluorescent or pigmented label or contains a moiety that participates in a reaction to form a fluorescent or pigmented product, the candidate compounds linked to solid supports can be separated from non-candidate (i.e., non-binding) compounds using a cell sorter; such instruments, such as fluorescent-activated cell sorters (FACS), are well known in the art. After sorting, individual solid supports can be isolated, the chimeric protein eluted from the bound compound of interest, and the compound characterized. Alternatively, for solid supports containing a tag identifying the immobilized compound, the tag may be "read" to obtain information about the compound. Solid supports may also be sorted by hand, provided the particle is large enough to be so manipulated.

The secondary binding partner may alternatively be joined to a solid support, such as a magnetic sphere to facilitate purification of the binding partner complex. In such a case, application of a magnetic field will allow the beads to be washed free of unbound compounds prior to isolation and purification. Such a strategy may be employed even when the library members are themselves bound to a solid support.

In another aspect, the chimeric protein may be immobilized on a solid support in such a way as to allow binding of the binding partner of the first domain with a compound in solution. Immobilization may be performed by formation of an antibody:antigen binding complex partner between the solid support (e.g., with an anti-IgG antibody covalently joined thereto, or through use of Protein G or Protein A) and the variable region or antigenic epitope of the second domain of the chimeric protein. After contacting the immobilized chimeric protein with a sample suspected of containing one or more compound of interest, other components of the sample may be washed away and the compound(s) then eluted to produce an enriched population of candidate compounds.

In yet another aspect, the present invention is directed to diagnostic assay methods for the detection or quantification of a member of a binding pair, for example, a receptor, cytokine, enzyme, antibody, ligand or the like, in a sample. The method includes contacting a chimeric protein, as described above, with a sample suspected of containing the compound of interest under conditions permitting the binding of the first domain of the chimeric protein and the compound. Preferably, the compound is immobilized on a solid support so that a chimeric protein:compound binding partner complex is formed after said contacting step. The solid support-bound binding complex can then be washed and the complex detected by interaction of the second domain of the chimeric protein with a directly or indirectly labeled ligand, such as a secondary antibody.

In yet another aspect, the invention is directed to methods for rapidly screening members of a chemical combinatorial library. The library members may be contained in solution or may be immobilized on solid phase supports, whether synthetic or biological. The compounds to be screened may be peptides, oligonucleotides, saccharides, mixtures or analogs of any of these molecular types, other organic molecules, or non-organic compounds which are desired to be preliminarily screened on the basis of their interaction with a binding partner. The relationship between the binding partner and the compound to be screened may be, for example, antibody:antigen, ligand:receptor, enzyme:substrate or any other specific binding interaction between a protein binding partner and a compound. It will be understood that such methods may be used to screen and aid in the identification of analogs and non-naturally-occurring mimics or variants of the natural ligands of these binding partners. Additionally, the specific binding partner contained in the chimeric protein need not be a natural ligand but may itself be an analog of a naturally-occurring ligand.

In this aspect of the invention, the members of the combinatorial library are contacted with the chimeric protein under conditions favoring the binding of the binding partner contained in the first domain of the chimeric protein with a ligand. It is preferred that the chimeric protein be joined to at least another chimeric protein, either identical or different, to form a multimer, most preferably a dimer, joined together, for example, one or more disulfide linkage. In this form, the chimeric protein is at least bivalent with respect to the specific binding partner of the first domain and therefore may have the potential to bind a given compound at more than one location, and more strongly than the monomeric form or which the solid support containing monomeric compounds closely packed on the surface of the support. This is particularly true when the compound itself is in multmeric form. Use of chimeric proteins in multimeric form can be of particular advantage in detecting the presence of low- or medium-affinity candidate compounds from within the library; these compounds may have a completely different structure than the high affinity compounds, and elucidation of alternative ligand structures may yield information valuable in the later design of diverse higher affinity ligands with different chemical, biochemical or physical characteristics.

The chimeric protein can then be used to isolate or detect the library members to which it has bound through a second domain of the chimeric protein comprising at least one region of an immunoglobulin molecule which is able to specifically bind with an antigen or an antibody, wherein the molecule recognized by the first domain is different than the molecule recognized by the second domain. If the members of the combinatorial library are joined to a solid support, the solid support can be washed free of any unbound chimeric protein and the second domain of the specifically bound chimeric protein molecules allowed to bind with a labeled binding partner, such as a fluorescently, enzyme-labeled radioactively, or dye-labeled secondary antibody. Subsequent detection of the label-associated solid support particles permits identification and isolation of the compound of interest.

It will be apparent in light of the instant disclosure, that, if the compounds being screened are peptides, a chimeric protein can be made having a first domain including a known peptide, for example, the extracellular portion of a cell surface receptor for a specific humoral factor. If analogs to the cell surface receptor are desired, one may employ the methods disclosed herein to isolate compounds from a peptide combinatorial library able to bind the receptor. Upon determination of the structure of such a compound, this new compound can be made the "binding partner" portion of the first domain of a new chimeric protein, and the new chimeric protein used to screen the same or a different combinatorial library for analogs of the receptor. It will also be apparent that this method may be employed to obtain "binding analogs" of a given compound even when the structure of the natural binding partner for a given compound is not known.

Thus, another aspect of the present invention is a method of making a chimeric protein useful in the screening of compounds for their ability to bind a given peptide, comprising the construction of a recombinant plasmid containing a nucleotide sequence encoding at least one constant (C) or variable (V) region of an immunoglobulin chain positioned downstream from a promoter sequence. While it is preferred that the portion of the gene encoding the immunoglobulin chain correspond to either the amino terminal region or the carboxy terminal region of the mature immunoglobulin molecule, all that is necessary is that the nucleotide sequence encode a portion of at least one C or V region recognizable by an antigen or antibody. The portion of the nucleotide sequence encoding the immunoglobulin (C) and/or (V) region have a region at either its 3' or 5' end one or more restriction endonuclease sites for insertion of a DNA fragment within the coding sequence of the immunoglobulin chain. Preferably, the region contains a restriction cluster of about four or more different restriction endonuclease cleavage sequences for facile cloning. If this restriction cluster is located at the 5' side of the immunoglobulin sequences, the restriction cluster must be positioned between the immunoglobulin sequences and the promoter sequence. Also, the cloned immunoglobulin chain portion preferably contains the nucleotide sequence encoding the "hinge" region of an immunoglobulin chain; such a region usually comprises a proline-containing region having at least one cysteine residue. It will be understood that reference to the 3' or 5' side of a particular nucleotide sequence or sequence region refers to the coding strand of the DNA molecule unless indicated otherwise herein. Preferably, the immunoglobulin chain contains sequences derived from an immunoglobulin heavy (H) chain which include constant (C) region nucleotide sequences.

Such a vector can be regarded as a "cassette holder"; that is this portion of the vector is capable of receiving many interchangeable nucleic acid fragments ("cassettes") encoding portions of receptors, ligands, or other binding partners. The fragments should be engineered or selected to contain restriction sites matching those at one end of the immunoglobulin sequences; in such a case, ligating the binding partner fragment into the vector is trivial. Care must be taken, however, to ensure that the binding partner gene fragment ("cassette") is placed in the same reading frame as the immunoglobulin portion of the chimeric gene. This can be accomplished, if necessary thorough the construction and use of appropriate oligonucleotide primers or linkers containing a number of bases sufficient to place the cassette in the same reading frame as the immunoglobulin portion of the chimeric gene. If desired, one or more of the primers or linkers may also be constructed to incorporate nucleotide sequences comprising one or more restriction endonuclease cleavage site for facile cloning and interchange of subunits of the binding partner.

Suitable cassettes can be easily constructed; as an example by using PCR or another nucleic acid amplification method. Such methods generally utilize at least two primers directed to different strands and to different locations 5' and 3' (with respect to the coding strand) of the gene portion to be cloned. When the gene fragment, encoding, for example, a portion of a receptor molecule is to be cloned at the 5' end of the gene expressing the chimeric protein, the primer directed to the 5' portion of the nucleic acid to be amplified will generally contain an ATG start codon. An example of such a primer is shown in the Examples below. Such a primer can also be directed to the untranslated region of the gene 5' of the ATG to be amplified, in order to ensure that other transcription or translation regulatory sequences (such as the TATA box or a ribosomal binding sequence (RBS)) are also included in the amplified nucleic acid. An example of a consensus eukaryotic RBS is: SEQ ID NO: 19; 5'-GCCRCCATGG-3', where "R" is either A or G. The primer may be directed to sequences to the 5' side of such regulatory sequences, may be directed to some or all of such sequences themselves, or may not be designed to amplify such sequences at all. Those of skill in the art will, in light of this disclosure, recognize that for a given binding partner one of these options may optimize the expression of the chimeric gene; determination of which of these three options may be optimal is a matter of routine screening easily performed by those of skill in the art.

The recombinant vector is preferably capable of replication and expression of the chimeric protein in eukaryotic cells; thus the vector will preferably contain an origin of replication allowing the episomal replication in such cells. In such a case, the promoter directly upstream from the cloned synthetic gene encoding is the chimeric protein will be one capable of directing transcription in a eukaryotic host. It is also preferable that the vector and host cell be chosen so as to allow the vector to be replicated and transcribed at high copy number by the eukaryotic cell.

Expression of such chimeric proteins in eukaryotic cells allows the cell to treat the expressed chimeric protein much like an immunoglobulin molecule. Thus, the chimeric protein may be glycosylated, permitted to form dimers or other multimeric forms and transported to the cell surface for secretion just as a native immunoglobulin would. This also allows the chimeric protein to be harvested from the tissue culture supernatant without lysing the cells, therefore facilitating purification. As described below, Applicant has demonstrated the feasibility of this approach by cloning and expressing the chimeric protein as a secreted product in African green monkey cells.

Purification of the chimeric protein can be performed by exploiting one of the two specific binding domains of the chimeric protein in a minimum of steps by affinity chromatography; for example, by using immobilized Protein G or an immobilized anti-IgG antibody. The chimeric protein can then be eluted from the affinity matrix for use. Alternatively, the cell-free tissue culture medium containing the chimeric protein can be used without further purification.

In embodiments of the invention employing non-biological solid supports, these solid supports are any insoluble or semisoluble matrix on which chemical compounds, including antibodies and other proteins and members of a combinatorial library, can be joined. Such matrices include: nitrocellulose; cellulose derivatives; nylon; controlled pore glass; polystyrene or polyacrylamide derivatives; dendromeres, magnetic beads; particles or microspheres.

Additional embodiments of the present invention are directed to methods of using the chimeric proteins described herein. One such method of use—that of utilizing the first domain of the chimeric protein to bind solid supports displaying a compound or library member of interest, identifying the bound chimeric protein by directing a labeled ligand to the second domain of the protein, detecting the label, and sorting the identified solid supports—has been described above. The chimeric protein may also be used in an application in which the candidate compounds are coated onto a microtiter well, the chimeric protein added, and a directly or indirectly labeled ligand directed to the second chimeric protein domain used to identify the bound chimeric protein. An example of indirectly labeled ligands are antibodies labeled with an enzyme, such as horseradish peroxidase or alkaline phosphatase, which can then be exposed to a substrate in a colorimetric reaction to indicate the presence of the compound of interest. The converse of this scheme may also be employed in which the chimeric protein is immobilized and the library members are used to bind thereto. In the interests of increased assay throughput, an initial screen can be performed using mixtures of different compounds, and subsequent screens can then identify the specific compounds of interest.

Additional embodiments can be found in the examples and in the claims which conclude this specification.

EXAMPLES

Example 1

Vector Construction

The commercially available vector pcDNA3 was purchased from Invitrogen Corp., San Diego, Calif. This eukaryotic/prokaryotic shuttle vector, which is 5.4 kb in length, includes the following elements: the cytomegalovirus (CMV) eukaryotic promoter and the T7 bacteriophage promoter, both promoting transcription in the clockwise direction; the SP6 bacteriophage promoter, promoting transcription in the opposite direction; a polylinker containing restriction sites for, in order from 5' to 3' with respect to the cloned sequences described below,: Hind III, Kpn I, Bam H1, BstX I,EcoR I, EcoR V, BstX I, Not I, XhoI, Xba I and Apa I; the SV40 eukaryotic origin of replication, the ColE1 bacterial episomal origin of replication, the ampicillin resistance gene, and the neomycin resistance gene.

This plasmid was linearized using the restriction enzymes Not I and Xho I, as follows. A 200 $\mu$l reaction mixture containing 300 $\mu$g/ml pcNDA3 DNA, 600 units/ml each of Not I and Xho I (New England Biolabs), 10 mM Tris HCl (pH 7.9), 10 mM MgCl$_2$, 50 mM NaCl, 1 mM DTT and 100 $\mu$/ml BSA (bovine serum albumin) was incubated at 37° C. overnight. The DNA fragments were separated on a 1% agarose gel using TBE (89 mM Tris (pH 8.0), 89 mM boric acid, 2 mM EDTA (ethylene diamine tetraacetic acid)). The large linearized DNA fragment was excised from the gel, the gel slice crushed and the DNA extracted by adsorption on glass particles, and purified by precipitation in ethanol. The purified DNA fragment was resuspended in TE (10 mM Tris (pH 7.5, 1 mM EDTA), and the concentration of the purified DNA fragment ascertained by determining the absorbance of the solution at 260 nm in a spectrophotometer. The isolated DNA was stored at –20° C. until use.

Genomic mouse DNA was prepared from a lysate of frozen NIH3T3 cells (a mouse fibroblast cell line. An aliquot of NIH3T3 cells (5×10$^5$) were centrifuged at 2500 xg for 4 minutes and washed three times with PBS (phosphate-buffered saline). The cells were resuspended in 10 $\mu$l of a hypotonic buffer (50 mM KCl, 10 mM Tris HCl (pH 8.4), 1.5 mM MgCl$_2$) containing 0.5% (v/v) TWEEN® 20 non-ionic surfactant and 10 $\mu$g of proteinase K, and incubated at 56° C. for 45 minutes. The crude lysate was then incubated at 95° C. for 10 minutes, and finally stored at 4° C.

Cloning of the IgG1 immunoglobulin fragment

The carboxy-terminal mouse DNA sequences encoding the constant region $C_H2$, $C_H3$ and hinge domains of the murine IgG1 heavy chain were amplified from NIH3T3 genomic DNA using PCR. The following oligonucleotide primers were synthesized to be complementary to corresponding portions of the immunoglobulin gene. The underlined portion of SEQ ID NO. 1 corresponds to a Not I restriction endonuclease cleavage site, and the bolded underlined portion of SEQ ID NO. 2 corresponds to an Xho I restriction endonuclease cleavage site.

Sense primer (SEQ ID NO. 1)

5'--AGCTTCGA<u>GC GGCCG</u>CCGTG CCCAGGGATT GTGGT-
    TGTAA G--3'

Antisense primer (SEQ ID NO. 2)

5'--GATC<u>CTCGAG</u> TCATTTACCA GGAGAGTGGG AGAG-
    GCT--3'

The PCR reaction was set up by adding the following reagents to a sterile 0.6 ml microfuge tube in the following order: ten microliters of 10×PCR Buffer II (100 mM Tris HCl (pH 8.3), 500 mM KCl), 6 $\mu$l of 25 mM MgCl$_2$, 2 $\mu$l of a 10 mM solution of each dNTP, 2.5 $\mu$l of 10 $\mu$M mouse IgG1 sense primer (SEQ ID NO. 1), 2.5 $\mu$l of 10 $\mu$M mouse IgG1 antisense primer (SEQ ID NO. 2), 0.5 $\mu$l (2.5 units) of AMPLITAQ® thermostable DNA polymerase (Perkin Elmer Corp.), 66.5 $\mu$l ultra pure water, and one wax bead. The reaction mixture was incubated at 70° C. until the wax bead melted, then 10 $\mu$l of the NIH3T3 lysate was added. The reaction mixture was placed in a Perkin Elmer 480 Thermal Cycler, and the cycler programmed to run 30 cycles under the following conditions: 1 minute at 94° C, 55° C. for 1 minute, 72° C. for 1.5 minutes, and held at 4° C. until use.

The amplified DNA from the PCR reaction was gel purified by electrophoresis through a 1% agarose gel in TBE. The DNA band corresponding to the amplified DNA was excised from the gel, and eluted in 40 $\mu$l of water as above. The purified amplified IgG1 gene fragment was then digested with the restriction enzymes Not I and Xho I as described above. The restriction digest was run on a 1% agarose/TBE gel, the approximately 1 kb fragment was excised from the gel and the DNA eluted from the gel slice in 40 $\mu$l of water. The yield was determined by measuring the optical density of the solution at 260 nm on a Beckman DU600 spectrophotometer.

The Xho I- and Not I-digested IgG1 PCR product was ligated into the Xho I- and Not I- digested pcDNA3 vector as follows. The ligation reaction was performed in a total volume of 20 $\mu$l containing approximately 100 ng pcDNA3 and 100 ng of the IgG1 PCR fragment. This was incubated in 50 mM Tris-HCl (pH 7.8), 10 mM MgCl$_2$, 10 mM DTT, 1 mM ATP, 25 $\mu$g/mL BSA with 1 unit of DNA ligase at room temperature overnight.

A 1 $\mu$l aliquot of the ligation mix was used to transform Stratagene Epicurean Coli SURE® Competent Cells (these cells have the genotype: e14-(McrA-) Δ(mcrCB-hsdSMR-mrr)171 endA1 supE44 thi-1 gyrA96 relA1 lac recB recJ sbcC umuC::Tn5 (Kan$^r$) uvrC [F' proAB lacI$^q$ZΔM15 TN10 (Tet$^r$)] and are supplied in a transformation buffer). A 50 $\mu$l aliquot of thawed cells was placed on ice with 1 $\mu$l of the ligation reaction mixture for 30 minutes, followed by a heat shock at 42° C. for 45 seconds. 500 $\mu$l of Luria broth was added and the cells incubated at 37° C. for 1 hour with shaking. The transformants were plated onto LB (Luria broth plates containing 50 $\mu$g/mL ampicillin; pcDNA3 carries the β-lactamase gene, which confers resistance to ampicillin whereas untransformed cells do not contain this gene. Representative transformants were used for the preparation of vector DNA by standard "miniprep" procedures, as described in Sambrook et al., *Molecular Cloning*: A Laboratory Manual (Cold Spring Harbor Press 2d ed. 1989).

Vector DNA was digested with Not I and Xho I and resolved on a 1% agarose/TBE analytical gel to check for the presence of the cloned, PCR-derived mouse IgG1 constant and hinge region. Vector DNA from clones containing Not I/Xho I inserts was purified as described above prior to nucleic acid sequencing.

Nucleic acid sequencing was performed using Applied Biosystems' PRISM® Dye Terminator Cycle Sequencing Ready Reaction Kit according to the manufacturer's instructions. This protocol employs fluorescently-labeled dideoxyribonucleotides as chain terminators for the sequencing reaction, and the results are automatically recorded. The sequencing reaction mixtures were run on a a 4% acrylamide denaturing gels containing urea for 10 hours and the entire sequence of the fragment determined. After verification that a clone contained the proper sequence, a large-scale vector preparation was done. The new vector, containing the mouse IgG1 $C_H2$, $C_H3$, and hinge regions, was termed pcDNA3-IgG1, disclosed herein as SEQ ID NO: 5. It will be recognized that this vector may be used to clone DNA fragments whose 3' end incorporate a Not I restriction endonuclease site.

Applicant has also found that a corresponding segment of the IgG2b heavy chain containing the $C_H2$, $C_H3$, and hinge regions can be cloned in a similar manner. These IgG2b chimeric proteins may be preferable for certain applications.

Since the primary structure of many immunoglobulins is known, it will be clear to those of skill in the art that a similar strategy may be employed to clone DNA fragments encoding receptors and other peptide binding partners at a position 3' (rather than 5', as above) to the immunoglobulin-encoding portion of the chimeric gene. Upon expression, the result would be a chimeric protein containing the binding partner at its carboxy terminus. This conformation not only would allow the possibility of presenting the binding partner to the test or library compounds in both amino- and carboxy-oriented aspects, but provides the possibility of including a desired variable region of an immunoglobulin chain, for example a monoclonal antibody, as part of the second domain of the chimeric protein. Moreover, if the $V_H$, and at least the $C_H2$, $C_H3$ immunoglobulin regions and the binding partner were included in the chimeric protein, it would be reasonably expected in light of the present disclosure that such a chimeric protein might not only have one specific binding region within the second domain, but may in fact have two.

Cloning of tumor necrosis factor receptor (TNF-R) into pcDNA 3-IgG1

The DNA fragment encoding the extracellular portion of the human tumor necrosis factor-α receptor (TNF-R) was obtained from PCR amplification of total RNA cDNA from human peripheral blood mononuclear cells (PBMC). RNA was collected from the PBMCs using standard procedures. The RNA was reverse transcribed in a reaction micture containing 1 μg PBMC whole RNA, 12.5 mM each dNTP, 50 mM Tris-HCl (pH 8.3), 40 mM KCl, 5 mM DTT (dithiolthreitol), 20 pmoles of a random deoxyribonucleotide hexamer, and 100 units SUPERSCRIPT® reverse transcriptase. The reaction mixture was incubated at 42° C. for 1 hour, then at 95° C. for 5 minutes, and stored at 4° C. until use.

PCR reactions of the PBMC cDNA preparation were performed using the following primers.

TNF-R sense primer (SEQ ID NO: 3):

5'--GATCGGATCC <u>ATG</u>GGCCTCT CCACCGTGCC TGAC--3'

TNF-R antisense primer (SEQ ID NO: 4):

5'--AGCTTCGAGC GGCCGCTGTG GTGCCTGAGT CCT- CAGTGCC--3'

The primer having SEQ ID NO: 3 incorporates a ATG start codon (underlined) and a Bam HI site (bolded) into the amplified nucleic acid.

PCR reactions were performed as described previously. The TNF-R PCR product and the pcDNA3-IgG1 were each digested with BamHI and Not I, and the larger DNA fragments of each reaction were gel purified as described above. The purified TNF-R DNA fragment and vector fragment were then ligated together as described above to yield the chimeric protein expression vector pcDNA3-IgG1-TNF-R, disclosed herein as SEQ ID NO: 6, having the TNF-R fragment in the proper orientation. Vector construction was confirmed by diagnostic restriction digestion and nucleic acid sequencing. Large scale vector preparations were made from the transformed *E. coli* clone.

Example 2
Transfection of African green monkey cells with pcDNA3-IgG1-TNF-R, and expression of the chimeric protein The host cells chosen to demonstrate expression of the chimeric protein of the present invention were COS-7 African green monkey kidney cells. This cell line can be used for large scale production of heterologous proteins by transfection and expression of a recombinant vector having appropriate regulatory elements, such as pcDNA3-IgG1-TNF-R.

COS-7 cells were grown in Dulbecco's Modified Eagle Medium supplemented with 4500 mg/nl D glucose, 584 mg/ml L-glutamine, and 10% fetal bovine serum (FBS). For transformations, cells were seeded at $1-2 \times 10^5$ cells/ml and incubated at 37° C. at 5% $CO_2$ until 50–70% confluent. By percentage confluent is meant the percentage of the substrate, such as the microtiter dish bottom, that is occupied by cells. The cells were then transfected as follows. For each transfection a solution was made by mixing 20 μl LIPOFECTIN® (a cationic lipid preparation containing a 1:1 molar ratio of DOTMA (N-[1-(2-, 3-dioleyloxy)propyl]-N, N,N trimethylammonium chloride) and DOPE (dioleyl phosphatidylethanolamine) with 100 μl serum-free medium and the solution was allowed to stand at room temperature for 30 minutes. One to two microliters of the pcDNA3-IgG1-TNF-R solution was also diluted into 100 μl serum-free emdium. The two solutions were combined, mixed gently and incubated at room temperature for 10–15 minutes. Cells were then overlayed with the DNA-LIPOFECTIN® mixture and incubated overnight at 37° C. Trasfection mixture was then removed and replaced with medium. Expression of the pcDNA-IgG1-TNF-R vector was constitutive in the COS-7 cells. The chimeric protein is secreted into the culture media, and can be harvested by decanting or aspirating the cell-free media. Cell-free supernatant was assayed for secretion of the chimeric protein at 48–72 hours following transfection.

Example 3
Screening of compounds coated within microtiter wells using an immunoglobulin-binding partner chimeric protein Following expression of the chimeric protein, the cell-free culture medium was harvested and tested for the presence of the fusion protein. The wells of a plastic microtiter dish were coated with a preparation of TNFα by addition of 2 ng of recombinant TNFα per well in PBS and overnight incubation at 4° C. or 2 hours at room temperature. The wells were then washed three times with wash buffer (PBS containing 0.05% (v/v) TWEEN®-20 non-ionic detergent. Following the wash, the wells were blocked to prevent non-specific binding with PBS containing 1% (w/v) BSA and 0.05% TWEEN®-20 non ionic detergent (blocking buffer). The wells were again washed as before. The culture media was serially diluted two-fold 11 times in the blocking buffer and 50 μl of each dilution (and the undiluted media) was added to the coated, blocked wells. A set of uncoated wells also received the diluted cell-free media. Microtiter plates were then incubated for 2 hours at room temperature, then washed three times as before. The presence of the bound chimeric protein was assayed using 100 μl of a 1:5000 dilution of an anti-mouse IgG antibody labeled with horseradish peroxidase (ELISA).

Color development was commenced with addition of 100 μl of a commercially obtained chromogenic horseradish peroxidase (HRP) substrate (TMB Color Reagent, Kirkegaard & Perry Laboratories) to each of the microtiter wells. The plates were incubated at room temperature for up to 20 minutes. Color development in this assay system may be terminated by addition of 100 microliters of a stop solution (Kirkegaard & Perry, product code 50-85-05) to each well.

The control wells showed no color development. By contrast, the wells in which a TNF/TNF-R complex had been formed showed a distinct blue to purple color formation. The absorbance of each dilution at 450 nm was measured, the absorbance at 650 nm was subtracted, and the results were plotted. The results are shown below.

Potential sites of non-specific binding of protein to the SEPHAROSE® beads was blocked by resuspending and incubating the two bead slurries (TNF and control) in 10 volumes of 1% (w/v) BSA and in TBST (20 mM Tris-HCl (pH 7.5), 150 mM NaCl and 0.05% (v/v) TWEEN® 80 non-ionic surfactant) for 15 minutes at 5 room temperature.

Forty microliters of the TNF and control SEPHAROSE® beads were each exposed to 100 μl of tissue culture supernatant from either untransfected or the pcDNA3-IgG1-TNF-R transformed COS-7 cells and incubated at room temperature for 1 hour. The beads were then washed with TBST.

Detection of the bound chimeric protein was accomplished through the use of a secondary anti-mouse IgG1 antibody coupled to alkaline phosphatase (AP). The alkaline phosphatase-coupled antibody, and its chromogenic substrate was obtained from a commercially available kit, the PROTOBLOT® II AP System (Promega Corp.), and used in accordance with the manufacturer's directions. A solution of AP-anti-mouse IgG (1 mg/ml) was diluted 1:5000 into Tris-buffered saline (TBS; 20 mM Tris-HCl (pH 7.5), 150 mM NaCl). One hundred microliters of this solution was added to the aliquots of SEPHAROSE® beads and incubated at room temperature for 1 hour. The beads were then washed three times in TBS.

Color development was commenced with addition of 100 μl WESTERN BLUE® chromogenic AP substrate to each of the aliquots of SEPHAROSE® beads.

| Dilution | 1:1 | 1:2 | 1:4 | 1:8 | 1:16 | 1:32 | 1:64 | 1:128 | 1:256 | 1:512 | 1:1024 | 1:2048 |
|---|---|---|---|---|---|---|---|---|---|---|---|---|
| Transfected medium | 1.147 | 1.199 | 1.161 | 0.901 | 0.747 | 0.406 | 0.259 | 0.166 | 0.112 | 0.085 | 0.071 | 0.037 |
| Untransfected Medium | 0.101 | 0.028 | 0.028 | 0.053 | 0.037 | 0.055 | 0.053 | 0.0764 | 0.044 | 0.063 | 0.075 | 0.057 |
| No TNF Control | 0.136 | 0.032 | 0.030 | 0.035 | 0.038 | 0.035 | 0.029 | 0.023 | 0.028 | 0.027 | 0.029 | 0.040 |

The results indicate that neither the control wells containing tissue culture media from untransfected cells, nor the control wells containing the media from transfected cells in the absence of TNF gave an indication of color formation; i.e. specific binding between the chimeric protein and the TNF binding partner. However, the media from cells transfected with the vector encoding the chimeric protein was able to bind to wells coated with TNF, and gave a titration curve indicating the presence of specific target binding.

Example 4
Screening of particle-bound compounds using an immunoglobulin-binding partner chimeric protein Recombinant TNFα (obtained from R & D Systems) was immobilized on cyanogen bromide-activated SEPHAROSE® CL 4B agarose beads as follows. A 0.5 ml aliquot of cyanogen bromide-activated SEPHAROSE® 4B was washed with ice-cold 0.1N HCl. Ten micrograms of TNFα were dissolved in 10 μl PBS, then added to 100 μl of a solution of 0.1M HCO₃ and 0.5M NaCl. This was mixed with 100 μl of the washed, activated SEPHAROSE® beads and the suspension incubated at room temperature for 2 hours.

The unreacted cyanogen bromide-activated sites were blocked by the addition of 500 μl of 50 mM glycine (pH 8.0) to the TNF-coupled SEPHAROSE® beads. The same amount of the glycine solution was added to 100 μl of washed, uncoupled SEPHAROSE® as a negative control.

These were incubated at room temperature for 20 minutes. Color development in this assay system may be terminated by washing the beads with water. Aliquots of each SEPHAROSE® bead mixture were observed under a microscope using a 10×objective lens. The control beads remained colorless. By contrast, the beads in which a TNF/TNF-R complex had been formed were stained with a distinct blue to purple color.

Example 5
Construction of Additional Fusion Peptides

Using the pCDNA3-IgG1 "cassette holder" and the same strategy employed in the Examples described above, additional individual chimeric proteins were made having, at the amino terminal regions, extracellular ligand-binding portions of the erythropoietin receptor, FAS (a receptor of the Nerve Growth Factor family having properties similar to TNFα-R), the interleukin 4 receptor, and the interleukin 6 receptor. The nucleotide sequences for these receptors was obtained from the GENBANK nucleotide sequence database. The nucleotide sequences of other binding partners can be obtained from published or database sources, or can be obtained by direct peptide sequencing of an isolated protein.

Primers designed to amplify the extracellular portions of the indicated receptors were employed to obtain PCR-amplified, "clonable" double-stranded DNA. As above, sense primers incorporated a BamH1 site just prior to the ATG initiation codon, and antisense primers incorporated a Not I restriction site after the termination codon. Primer sets (with the initiation codon of the sense strand underlined) and the amplified DNA sequences (coding strand sequence only) were as follows:

ERYTHROPOIETIN RECEPTOR

Sense primer
SEQ ID NO: 7

5'-GATCGGATCC<u>ATG</u>GACCACCTCGGGGCGTCCCTC-3'

Antisense primer
SEQ ID NO: 8

5'-AGCTTCGAGCGGCCGCGGGGTCCAG-GTCGCTAGGCGTCAG-3'

EPO Receptor DNA sequence amplified:

SEQ ID NO:9
5
ATGGACCACCTCGGGGCGTCCCTCTGGCCCCAGGTCGGCTCCCTTTGTCTCCT
GCTCGCTGGGGCCGCCTGGGCGCCCCCGCCTAACCTCCCGGACCCCAAGTTCG
AGAGCAAAGCGGCCTTGCTGGCGGCCCGGGGGCCCGAAGAGCTTCTGTGCTTCA
CCGAGCGGTTGGAGGACTTGGTGTGTTTCTGGGAGGAAGCGGCGAGCGCTGG
GGTGGGCCCGGGCAACTACAGCTTCTCCTACCAGCTCGAGGATGAGCCATGGA
AGCTGTGTCGCCTGCACCAGGCTCCCACGGCTCGTGGTGCGGTGCGCTTCTGGTG
TTCGCTGCCTACAGCCGACACGTCGAGCTTCGTGCCCCTAGAGTTGCGCGTCA
CAGCAGCCTCCGGCGCTCCGCGATATCACCGTGTCATCCACATCAATGAAGTA
GTGCTCCTAGACGCCCCCGTGGGGCTGGTGGCGCGGTTGGCTGACGAGAGCGGC
CACGTAGTGTTGCGCTGGCTCCCGCCGCCTGAGACACCCATGACGTCTCACAT
CCGCTACGAGGTGGACGTCTCGGCCGGCAACGGCGCAGGGAGCGTACAGAGG
GTGGAGATCCTGGAGGGCCGCACCGAGTGTGTGCTGAGCAACCTGCGGGGCC
GGACGCGCTACACCTTCGCCGTCCGCGCGCGTATGGCTGAGCCGAGCTTCGGC
GGCTTCTGGAGCGCCTGGTCGGAGCCTGTGTCGCTGCTGACGCCTAGCGACCT
GGACCCC-3'

INTERLEUKIN 4 RECEPTOR

Sense primer
SEQ ID NO: 10

5'-GATCGGATCC<u>ATG</u>GGGTGGCTTTGCTCTGGGCTC-3'

Antisense primer
SEQ ID NO: 11

5'-AGCTTCGAGCGGCCGCGTGCTGCTC-GAAGGGCTCCCTGTA-3'

IL-4 Receptor DNA sequence amplified

SEQ ID NO:12
5
ATGGGGTGGCTTTGCTCTGGGCTCCTGTTCCCTGTGAGCTGCCTGGTCCTGCT
GCAGGTGGCAAGCTCTGGGAACATGAAGGTCTTGCAGGAGCCCACCTGCGTCT
CCGACTACATGAGCATCTCTACTTGCGAGTGGAAGATGAATGGTCCCACCAATT
GCAGCACCGAGCTCCGCCTGTTGTACCAGCTGGTTTTTCTGCTCTCCGAAGCCC
ACACGTGTATCCCTGAGAACAACGGAGGCGCGGGGTGCGTGTGCCACCTGCTC
ATGGATGACGTGGTCAGTGCGGATAACTATACACTGGACCTGTGGGCTGGGCA
GCAGCTGCTGTGGAAGGGCTCCTTCAAGCCCAGCGAGCATGTGAAACCCAGGG
CCCCAGGAAACCTGACAGTTCACACCAATGTCTCCGACACTCTGCTGCTGACCT
GGAGCAACCCGTATCCCCCTGACAATTACCTGTATAATCATCTCACCTATGCA

-continued
GTCAACATTTGGAGTGAAAACGACCCGGCAGATTTCAGAATCTATAACGTGACC

TACCTAGAACCCTCCCTCCGCATCGCAGCCAGCACCCTGAAGTCTGGGATTTCC

TACAGGGCACGGGTGAGGGCCTGGGCTCAGTGCTATAACACCACCTGGAGTG

AGTGGAGCCCCAGCACCAAGTGGCACAACTCCTACAGGGAGCCCTTCGAGCAG

CAC-3'

INTERLEUKIN 6 RECEPTOR

Sense primer
SEQ ID NO: 13

5'-GATCGAATTC<u>ATG</u>CTGGCCGTCGGCTGCGCGCTG-3'

Antisense primer
SEQ ID NO: 14

5'-AGCTTCGAGCGGCCGCATCTTGCACTGG-
GAGGCTTGTCGC-3'

IL-6 Receptor DNA sequence amplified

SEQ ID NO:15
ATGCTGGCCGTCGGCTGCGCGCTGCTGGCTGCCCTGCTGGCCGCGCCGGGAG

CGGCGCTGGCCCCAAGGCGCTGCCCTGCGCAGGAGGTGGCAAGAGGCGTGCT

GACCAGTCTGCCAGGAGACAGCGTGACTCTGACCTGCCCGGGGGTAGAGCCG

GAAG

ACAATGCCACTGTTCACTGGGTGCTCAGGAAGCCGGCTGCAGGCTCCCACCCC

AGCAGATGGGCTGGCATGGGAAGGAGGCTGCTGCTGAGGTCGGTGCAGCTCC

ACGACTCTGGAAACTATTCATGCTACCGGGCCGGCCGCCCAGCTGGGACTGTGCA

CTTGCTGGTGGATGTTCCCCCCGAGGAGCCCCAGCTCTCCTGCTTCCGGAAGA

GCCCCCTCAGCAATGTTGTTTGTGAGTGGGGTCCTCGGAGCACCCCATCCCTG

ACGACAAAGGCTGTGCTCTTGGTGAGGAAGTTTCAGAACAGTCCGGCCGAAGAC

TTCCAGGAGCCGTGCCAGTATTCCCAGGAGTCCCAGAAGTTCTCCTGCCAGTT

AGCAGTCCCGGAGGGAGACAGCTCTTTCTACATAGTGTCCATGTGCGTCGCCA

GTAGTGTCGGGAGCAAGTTCAGCAAAACTCAAACCTTTCAGGGTTGTGGAATCT

TGCAGCCTGATCCGCCTGCCAACATCACAGTCACTGCCGTGGCCAGAAACCCC

CGCTGGCTCAGTGTCACCTGGCAAGACCCCCACTCCTGGAACTCATCTTTCTAC

AGACTACGGTTTGAGCTCAGATATCGGGCTGAACGGTCAAAGACATTCACAAC

ATGGATGGTCAAGGACCTCCAGCATCACTGTGTCATCCACGACGCCTGGAGCG

GCCTGAGGCACGTGGTGCAGCTTCGTGCCCAGGAGGAGTTCGGGCAAGGCGA

GTGGAGCGAGTGGAGCCCGGAGGCCATGGGCACGCCTTGGACAGAATCCAGG

AGTCCTCCAGCTGAGAACGAGGTGTCCACCCCCATGCAGGCACTTACTACTAAT

AAAGACGATGATAATATTCTCTTCAGAGATTCTGCAAATGCGACAAGCCTCCCA

GTGCAAGAT-3'

FAS

Sense primer

SEQ ID NO: 16

5'-GATCGGATCC<u>ATG</u>CTGGGCATCTGGACCCTCCTACC-3'

Antisense primer

SEQ ID NO: 17

5'-AGCTTCGAGCGGCCGCGTTAGATCTG-
GATCCTTCCTCTTTGC-3'

FAS DNA sequence amplified

SEQ ID NO:18
ATGCTGGGCATCTGGACCCTCCTACCTCTGGTTCTTACGTCTGTTGCTAGATTA

TCGTCCAAAAGTGTTAATGCCCAAGTGACTGACATCAACTCCAAGGGATTGGAA

TTGAGGAAGACTGTTACTACAGTTGAGACTCAGAACTTGGAAGGCCTGCATCA

TGATGGCCAATTCTGCCATAAGCCCTGTCCTCCAGGTGAAAGGAAAGCTAGGG

ACTGCACAGTCAATGGGGATGAACCAGACTGCGTGCCCTGCCAAGAAGGGAAG

GAGTACACAGACAAAGCCCATTTTTCTTCCAAATGCAGAAGATGTAGATTGTGT

GATGAAGGACATGGCTTAGAAGTGGAAATAAACTGCACCCGGACCCAGAATAC

CAAGTGCAGATGTAAACCAAACTTTTTTTGTAACTCTACTGTATGTGAACACTG

TGACCCTTGCACCAAATGTGAACATGGAATCATCAAGGAATGCACACTCACCAG

CAACACCAAGTGCAAAGAGGAAGGATCCAGATCTAAC-3'

The amplified DNA fragments and pDNA3-IgG1 vector were both digested with BamH1 and Not I gel purified, as above, and then the amplified fragments ligated into the restriction-digested vector at a position immediately to the 5' side of the coding region for the hinge-IgG portion of the chimeric protein, again as described above. The recombinant vectors were then used to transfect COS-7 cells, as described above. In each case, the chimeric protein was secreted into the extracellular medium and the ability of each bind its intended ligand was verified.

Example 5

Structure of Secreted Chimeric Protein

Aliquots of the extracellular medium of individual chimeric proteins were electrophoresed on reducing and non-reducing SDS-PAGE gels, along with molecular weight standards and an anti GM-CSF monclonal antibody (bivalent) control. The antibody control and the chimeric proteins showed a marked increase in electrophoretic mobility on the reducing gel as compared to the non-reducing gel, indicating that the secreted chimeric proteins, like the antibody, are produced as disulfide-linked bivalent dimers.

The foregoing examples illustrate particularly preferred embodiments of the present invention, which is not to be construed as limited thereby. Further embodiments are contained throughout the specification and in the claims which follow. Applicant intends that the scope of the invention be determined from the embodiments described or suggested by the specification as a whole, and equivalents thereof.

What is claimed is:

1. A method of screening a plurality of test compounds for the ability to bind a specific binding partner comprising the steps:

a) contacting one or more test compounds with a chimeric protein containing two or more binding domains, wherein a first domain comprises a proteinaceous specific binding partner or a peptide analog thereof, and a second domain comprises at least a portion of an immunoglobulin chain having at least one region selected from the group consisting of:
        i) an antigenic determinant of an antigen, and
        ii) an immunoglobulin region capable of binding to an antigenic determinant,
    b) forming a binding partner complex between said chimeric protein and at least one of said test compounds,
    c) separating the complex from unbound chimeric proteins,
    d) contacting the binding partner complex with a directly or indirectly labeled secondary molecule capable of binding the second domain of said chimeric protein, and
    e) detecting said label as an indication of the presence of said test compound.

2. The method of claim 1 wherein said first and second domain of said chimeric protein are separated by an immunoglobulin heavy chain hinge region.

3. The method of claim 1 or 2 wherein said specific binding partner is selected from the group consisting of:
    a) an antigen,
    b) an antibody,
    c) an enzyme,
    d) an enzyme substrate,
    e) a receptor, and
    f) a ligand.

4. The method of claim 1 or 2 wherein said specific binding partner is selected from the group consisting of: growth hormone, human growth hormone, bovine growth hormone, parathyroid hormone, thyroxine, insulin A-chain, insulin-B chain, proinsulin, relaxin A-chain, leptin receptor, fibroblast growth factor, relaxin B-chain, prorelaxin, follicle stimulating hormone, thyroid stimulating hormone, luteinizing hormone, glycoprotein hormone receptors, calcitonin, glucagon, factor VIII, an antibody, lung surfactant, urokinase, streptokinase, tissue plasminogen activator, bombesin, factor IX, thrombin, hemopoietic growth factor, tumor necrosis factor alpha, tumor necrosis factor beta, enkephalinase human serum albumin, mullerian-inhibiting substance, gonadotropin-associated peptide, β lactamase, tissue factor protein, inhibitin, activin, vascular endothelial growth factor, integrin receptors, thrombopoietin, protein A or D, rheumatoid factors, NGF-β, platelet growth factor, transforming growth factor, TGF-α, TGF-β, insulin-like growth factor I and II, insulin growth factor binding proteins, CD4, CD8, DNase, RNase, latency associated peptide, erytbropoietin, osteoinductive factors, interferon-alpha, -beta and -gamma, colony stimulating factors, M-CSF, GM-CSF, G-CSF, stem cell factor, interleukins, IL1, IL-2, IL-3, IL-4, IL5, IL-6, IL-7, IL-8, IL-9, IL-10, IL-11, IL-12, superoxide dismutase, viral antigens, HIV envelope proteins, gp120, gp140, immunoglobulins, proteins encoded by the Ig supergene family, and naturally-occurring proteinaceous ligands or receptors thereof.

5. The method of claim 4 wherein said specific binding partner comprises at least a portion of the tumor necrosis factor alpha receptor.

6. The method of claim 4 wherein said specific binding partner comprises at least a portion of the endothelial growth factor receptor.

7. The method of claim 4 wherein said specific binding partner comprises at least a portion of the thrombopoietin receptor.

8. The method of claim 4 wherein said specific binding partner comprises at least a portion of the TGF alpha receptor.

9. The method of claim 4 wherein said specific binding partner comprises at least a portion of the TGF beta receptor.

10. The method of claim 4 wherein said specific binding partner comprises at least a portion of the erythropoietin receptor.

11. The method of claim 4 wherein said specific binding partner comprises at least a portion of the interferon gamma receptor.

12. The method of claim 4 wherein said specific binding partner comprises at least a portion of the GM-CSF receptor.

13. The method of claim 4 wherein said specific binding partner comprises at least a portion of the G-CSF receptor.

14. The method of claim 4 wherein said specific binding partner comprises at least a portion of the IL-4 receptor.

15. The method of claim 4 wherein said specific binding partner comprises at least a portion of the IL-6 receptor.

16. The method of claim 4 wherein said specific binding partner comprises at least a portion of the leptin receptor.

17. The method of claim 4 wherein said specific binding partner comprises at least a portion of the fibroblast growth factor receptor.

18. The method of claim 2 wherein said first domain is positioned to the amino terminal side of said second domain on said chimeric protein.

19. The method of claim 2 wherein said first domain is positioned to the carboxy terminal side of said second domain on said chimeric protein.

20. The method of claim 18 wherein said second domain comprises a $C_H3$ region of an immunoglobulin heavy chain.

21. The method of claim 20 wherein said second domain further comprises a $C_H2$ region of an immunoglobulin heavy chain.

22. The method of claim 1 or 2 wherein said test compounds are immobilized on a solid support.

23. The method of claim 1, 2 or 18 wherein said test compounds comprise a chemical combinatorial library.

24. The method of claim 23 wherein said library is comprised of members of the group selected of:
   a) naturally-occurring or non-naturally occurring amino acids,
   b) naturally-occurring or non-naturally occurring nucleotides,
   c) naturally-occurring or non-naturally occurring saccharides, and
   d) bi- or multifunctional small organic molecules.

25. The method of claim 22 wherein step c) is accomplished by washing the solid support to remove unbound chimeric protein.

26. The method of claim 1 or 2 wherein said chimeric protein is a first chimeric protein produced by expression, within a host cell, of a recombinant DNA open reading frame encoding said first chimeric protein.

27. The method of claim 26 wherein said host cell expresses said chimeric protein as a dimer joined by at least one disulfide linkage, said dimer containing at least two specific binding partners or peptide analogs thereof.

28. The method of claim 22 wherein said test compounds are contacted with chimeric protein comprising bivalent chimeric protein dimers containing at least two specific binding partners or peptide analogs thereof.

29. The method of claim 26 wherein said host cell further expresses DNA containing a second open reading frame encoding a second chimeric protein, said second chimeric protein comprising a first domain comprising a proteinaceous specific binding partner or a peptide analog thereof, and a second domain comprising at least a portion of an immunoglobulin chain having a region selected from the group consisting of:
   i) an antigenic determinant of an antigen, and
   ii) an immunoglobulin region capable of binding to an antigenic determinant, wherein said second chimeric protein contains at least a portion of an immunoglobulin light chain.

30. The method of claim 29 wherein said first chimeric protein and said second chimeric protein are linked by at least one disulfide bond to form a multimeric complex.

31. The method of claim 30 wherein the first domain of said first chimeric protein and said first domain of said second chimeric protein contain identical specific binding partners or peptide analogs thereof.

32. The method of claim 30 wherein the first domain of said first chimeric protein differs from said first domain of said second chimeric protein.

33. The method of claim 28 wherein at least one of said test compounds is present in the form of a multimer, and wherein said bivalent chimeric protein dimers bind said multimer more strongly than does a monomeric chimeric protein.

34. The method of claim 30 wherein at least one of said test compounds is present in the form of a multimer, and wherein said multimeric complex binds said multimer of test compound more strongly than do either said first or second chimeric protein individually.

35. The method of claim 26 wherein said host cell is a eukaryotic cell.

36. The method of claim 29 wherein said host cell is a eukaryotic cell.

37. The method of claim 26 wherein said open reading frame contains nucleotide sequences which direct the cell to add N-linked sugar residues to the chimeric protein expressed therefrom.

38. The method of claim 22 wherein said solid support is a cell.

39. The method of claim 22 wherein said solid support is a bacteriophage particle.

40. A method for screening one or more test compounds for the ability to bind a specific binding partner comprising the steps:
   a) immobilizing to a solid support a chimeric protein containing two or more distinct binding domains, wherein a first domain comprises a proteinaceous specific binding partner or a peptide analog thereof, and a second domain comprises at least a portion of an immunoglobulin chain having a region selected from the group consisting of:

i) an antigenic determinant of an antigen, and ii) an immunoglobulin region capable of binding to an antigenic determinant, wherein said chimeric protein is immobilized to the solid support by an interaction between said solid support and said second domain, b) contacting the immobilized chimeric protein with at least one test compound to form a binding partner complex comprising the chimeric protein and a test compound capable of binding to said specific binding partner, c) washing said solid support to separate the binding partner complex from unbound chimeric protein molecules, d) detecting said chimeric protein in said binding partner complex as an indication of the presence of said compound.

41. The method of claim 40 wherein said first and second domains of said chimeric protein are separated by an immunoglobulin heavy chain hinge region.

42. The method of claim 41 wherein said first domain is positioned to the amino terminal side of said second domain on said chimeric protein.

43. The method of claim 41 wherein said first domain is positioned to the carboxy terminal side of said second domain on said chimeric protein.

44. The method of claim 42 wherein said second domain comprises a $C_H3$ region of an immunoglobulin heavy chain.

45. The method of claim 44 wherein said second domain further comprises a $C_H2$ region of an immunoglobulin heavy chain.

46. The method of claim 40 or 41 wherein said immobilized chimeric protein is in the form of a disulfide-linked multimeric complex.

47. The method of claim 46 wherein said multimeric complex binds to two or more sites of said test compound.

48. The method of claim 40 or 41 wherein said test compounds are comprised of members selected from the group consisting of:
  a) naturally-occurring or non-naturally-occurring amino acids,
  b) naturally-occurring or non-naturally-occurring nucleotides,
  c) naturally-occurring or non-naturally occurring saccharides, and
  d) bi- or multifunctional small organic molecules.

49. The method of claim 40 wherein said chimeric protein is immobilized by a binding interaction between said chimeric protein and a moiety joined to the solid support, wherein the moiety is selected from the group consisting of:
  a) an antigen,
  b) at least a portion of an antibody,
  c) Protein G, and
  d) Protein A.

50. The method of claim 49 further comprising the step of eluting said test compound from said solid support before the detecting step d).

51. The method of claim 40 or 41 wherein the specific binding partner is selected from the group consisting of:
  a) an antigen,
  b) an antibody,
  c) an enzyme,
  d) an enzyme substrate,
  e) a receptor, and
  f) a ligand.

52. The method of claim 40 or 41 wherein said specific binding partner is selected from the group consisting of: growth hormone, human growth hormone, bovine growth hormone, parathyroid hormone, thyroxine, insulin A-chain, insulin-B chain, proinsulin, relaxin A-chain, leptin receptor, fibroblast growth factor, relaxin B-chain, prorelaxin, follicle stimulating hormone, thyroid stimulating hormone, luteinizing hormone, glycoprotein hormone receptors, calcitonin, glucagon, factor VIII, an antibody, lung surfactant, urokinase, streptokinase, tissue plasminogen activator, bombesin, factor IX, thrombin, hemopoietic growth factor, tumor necrosis factor alpha, tumor necrosis factor beta, enkephalinase human serum albumin, mullerian-inhibiting substance, gonadotropin-associated peptide, β lactamase, tissue factor protein, inhibitin, activin, vascular endothelial growth factor, integrin receptors, thrombopoietin, protein A or D, rheumatoid factors, NGF-β, platelet growth factor, transforming growth factor, TGF-α, TGF-β, insulin-like growth factor I and II, insulin growth factor binding proteins, CD4, CD8, DNase, RNase, latency associated peptide, erythropoietin, osteoinductive factors, interferon-alpha, -beta and -gamma, colony stimulating factors, M-CSF, GM-CSF, G-CSF, stem cell factor, interleukins, IL-1, IL-2, IL-3, IL-4, IL-5, IL-6, IL-7, IL-8, IL-9, IL-10, IL-11, IL-12, superoxide dismutase, viral antigens, HIV envelope proteins, gp120, gp140, immunoglobulins, proteins encoded by the Ig supergene family, and naturally-occurring proteinaceous ligands, receptors, or substrates thereof.

53. A method of screening a test compound for the ability to bind a specific binding partner comprising the steps:
  a) constructing a recombinant DNA vector capable of being expressed in a host cell, which vector comprises:
    i) an open reading frame containing a first sequence region encoding at least a portion of an immunoglobulin chain containing at least one region comprising an antigen-binding region, an antibody-binding region, or a hinge region, and
    ii) a promoter sequence positioned upstream of said open reading frame and capable of directing RNA transcription of said open reading frame within said host cell,
  wherein said open reading frame contains at least one restriction endonuclease site located between said first sequence region and said promoter sequence for cloning a second sequence region encoding a proteinaceous specific binding partner, provided said first and second sequence regions are cloned so as to preserve said open reading frame between said promoter sequence and a stop codon located at or after the 3' end of said first sequence region,
  b) inserting said second sequence region into the vector at said restriction endonuclease site,
  c) causing said vector to enter said host cell,
  d) incubating said host cell under conditions causing expression of a chimeric protein comprising amino acids encoded by said first and second sequence regions,
  e) separating said chimeric protein from said host cell,
  f) contacting a test compound with said chimeric protein under conditions favoring binding of said test compound with said specific binding partner of the chimeric protein, and
  g) specifically detecting the presence of a complex comprising said test compound bound to said chimeric protein as an indication of the presence of a test compound capable of binding to said specific binding partner.

54. The method of claim 53 wherein the constructing step further comprises inserting a third sequence region encoding at least a portion of the hinge region between said first and second sequence regions so as to preserve said open reading frame between said promoter sequence and said stop codon.

55. The method of claim 53 wherein said open reading frame encodes a chimeric protein containing two or more distinct domains wherein a first domain comprises a proteinaceous specific binding partner and a second domain comprises at least a portion of an immunoglobulin chain having a region selected from the group consisting of:
  i) an an antigenic determinant of an antigen, and
  ii) an immunoglobulin region capable of binding to an antigenic determinant.

56. The method of claim 55 wherein said specific binding partner is capable of binding a member of the group consisting of:
  a) an antigen,
  b) an antibody,
  c) an enzyme,
  d) an enzyme substrate,
  e) a receptor, and
  f) a ligand.

57. The method of claim 56 wherein said specific binding partner is capable of binding at least a portion of a compound selected from the group consisting of: growth hormone, human growth hormone, bovine growth hormone, parathyroid hormone, thyroxine, insulin A-chain, insulin-B chain, proinsulin, relaxin A-chain, leptin receptor, fibroblast growth factor, relaxin B-chain, prorelaxin, follicle stimulating hormone, thyroid stimulating hormone, luteinizing hormone, glycoprotein hormone receptors, calcitonin, glucagon, factor VIII, an antibody, lung surfactant, urokinase, streptokinase, tissue plasminogen activator, bombesin, factor IX, thrombin, hemopoietic growth factor, tumor necrosis factor alpha, tumor necrosis factor beta, enkephalinase human serum albumin, mullerian-inhibiting substance, gonadotropin-associated peptide, β lactamase, tissue factor protein, inhibitin, activin, vascular endothelial growth factor, integrin receptors, thrombopoietin, protein A or D, rheumatoid factors, NGF-β, platelet growth factor, transforming growth factor, TGF-α, TGF-β, insulin-like growth factor I and II, insulin growth factor binding proteins, CD4, CD8, DNase, RNase, latency associated peptide, erythropoietin, osteoinductive factors, interferon-alpha, -beta and -gamma, colony stimulating factors, M-CSF, GM-CSF, G-CSF, stem cell factor, interleukins, IL-1, IL-2, IL-3, IL-4, IL-5, IL-6, IL-7, IL-8, IL-9, IL-10, IL-11, IL-12, superoxide dismutase, viral antigens, HIV envelope proteins, gp120, gp140, immunoglobulins, proteins encoded by the Ig supergene family, naturally-occurring proteinaceous ligands, receptors, or substrates thereof, and peptide analogs thereof.

58. A method of screening a test compound for the ability to bind a specific binding partner comprising the steps:
  a) constructing a recombinant DNA vector capable of being expressed in a host cell, wherein said vector comprises:
    i) an open reading frame containing a first DNA sequence encoding at least a portion of an immunoglobulin chain, and
    ii) a promoter sequence positioned upstream of said open reading frame and capable of directing RNA transcription of said open reading frame within said host cell,
  wherein said open reading frame contains at least one restriction endonuclease site located at or near the 3' end of the first DNA sequence for cloning a second DNA sequence encoding specific binding partner polypeptide, provided said first and second DNA sequences are cloned so as to preserve said open reading frame between said promoter sequence and a stop codon located at or after the 3' end of said second DNA sequence,
  b) inserting said second DNA sequence into the vector at said restriction endonuclease site,
  c) causing said vector to enter said host cell,
  d) incubating said host cell under conditions causing the expression of a chimeric protein comprising amino acids encoded by said first and second DNA sequences,
  e) separating said chimeric protein from said host cell,
  f) contacting a test compound with said chimeric protein under conditions favoring binding of said test compound with said specific binding partner polypeptide of the chimeric protein, and
  g) specifically detecting the presence of a chimeric protein:test compound complex as an indication of the presence of a test compound capable of binding to said specific binding partner polypeptide.

59. The method of claim 58 wherein the constructing step further comprises inserting a third DNA sequence encoding at least a portion of an immunoglobulin heavy chain hinge region between said first and second DNA sequences so as to preserve said open reading frame between said promoter sequence and said stop codon.

60. The method of claim 59 wherein said vector of step c) encodes a chimeric protein containing two or more distinct domains, wherein a first domain comprises a specific binding partner polypeptide and a second domain comprises at least a portion of an immunoglobulin chain having a region selected from the group consisting of:
  i) an antigenic determinant of an antigen, and
  ii) an immunoglobulin region capable of binding to an antigenic determinant.

61. The method of claim 60 wherein said first DNA sequence encodes at least a portion of an immunoglobulin variable region.

62. The method of claim 60 or 61 wherein said specific binding partner polypeptide is capable of binding a member of the group consisting of:
  a) an antigen,
  b) an antibody,
  c) an enzyme,
  d) an enzyme substrate,
  e) a receptor, and
  f) a ligand.

63. The method of claim 60 or 61 wherein said specific binding partner polypeptide is capable of binding at least a portion of a compound selected from the group consisting of: growth hormone, human growth hormone, bovine growth hormone, parathyroid hormone, thyroxine, insulin A-chain, insulin-B chain, proinsulin, relaxin A-chain, leptin receptor, fibroblast growth factor, relaxin B-chain, prorelaxin follicle stimulating hormone, thyroid stimulating hormone, luteinizing hormone, glycoprotein hormone receptors, calcitonin, glucagon, factor VIII, an antibody, lung surfactant, urokinase, streptokinase, tissue plasminogen activator, bombesin, factor IX, thrombin, hemopoietic growth factor, tumor necrosis factor alpha, tumor necrosis factor beta, enkephalinase human serum albumin, mullerian-inhibiting substance, gonadotropin-associated peptide, β lactamase, tissue factor protein, inhibitin, activin, vascular endothelial growth factor, integrin receptors, thrombopoietin, protein A or D, rheumatoid factors, NGF-β, platelet growth factor, transforming growth factor, TGF-α, TGF-β, insulin-like growth factor I and II, insulin growth factor binding proteins, CD4, CD8, DNase, RNase, latency associated peptide, erythropoietin, osteoinductive factors, interferon-alpha, -beta and -gamma, colony stimulating factors, M-CSF, GM-CSF, G-CSF, stem cell factor, interleukins, IL-1, IL-2, IL-3, IL-4, IL-5, IL-6, IL-7, IL-8, IL-9, IL-10, IL-11, IL-12, superoxide dismutase, viral antigens, HIV envelope proteins, gp120, gp140, immunoglobulins, proteins encoded by the Ig supergene family, naturally-occurring proteinaceous ligands, receptors, or substrates thereof, and peptide analogs thereof.

* * * * *